United States Patent
Sampson et al.

(10) Patent No.: US 10,632,147 B2
(45) Date of Patent: *Apr. 28, 2020

(54) METHODS AND COMPOSITIONS FOR TREATING INFLAMMATORY DISORDERS

(71) Applicant: URGO US, INC., Fort Worth, TX (US)

(72) Inventors: Claire Sampson, Fort Worth, TX (US); Mark Sampson, Fort Worth, TX (US); Svetlana Panicheva, Fort Worth, TX (US); Cary Schockemoehl, Fort Worth, TX (US)

(73) Assignee: URGO US, INC., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/966,886

(22) Filed: Apr. 30, 2018

(65) Prior Publication Data
US 2018/0243335 A1 Aug. 30, 2018

Related U.S. Application Data

(63) Continuation-in-part of application No. 14/670,641, filed on Mar. 27, 2015, now Pat. No. 9,999,635, which is a continuation-in-part of application No. 14/494,261, filed on Sep. 23, 2014, now abandoned, which is a continuation of application No. 12/523,507, filed as application No. (Continued)

(51) Int. Cl.
*A61K 33/20* (2006.01)
*A61K 45/06* (2006.01)
*A61K 9/08* (2006.01)

(52) U.S. Cl.
CPC .............. *A61K 33/20* (2013.01); *A61K 45/06* (2013.01); *A61K 9/08* (2013.01)

(58) Field of Classification Search
CPC .......... A61K 33/20; A61K 45/06; A61K 9/08
See application file for complete search history.

(56) References Cited

U.S. PATENT DOCUMENTS

| | | |
|---|---|---|
| 6,333,054 B1 | 12/2001 | Rogozinski |
| 2002/0160053 A1 | 10/2002 | Yahagi et al. |
| 2003/0185704 A1 | 10/2003 | Bernard et al. |

(Continued)

OTHER PUBLICATIONS

Kruszewska et al, Mersacidin eradicates methicillin-resistant *Staphylococcus aureus* (MRSA) in a mouse rhinitis model, 2004, Journal of Antimicrobial Chemotherapy, 54, 648-653. (Year: 2004).*

(Continued)

*Primary Examiner* — Trevor Love
(74) *Attorney, Agent, or Firm* — Urgo US, Inc.

(57) ABSTRACT

The present invention provides methods for treating conditions that involve infection and/or inflammation, including acute and chronic inflammation, as well as delayed-type and immediate-type hypersensitivity. The invention in various embodiments provides methods for treating microbial infection and the associated inflammatory response, as well methods for treating inflammatory conditions that spawn or are susceptible to secondary microbial infection. Further, the invention provides methods for treating inflammation, such as chronic inflammation, without any associated microbial infection.

12 Claims, 3 Drawing Sheets

Related U.S. Application Data

PCT/US2008/051208 on Jan. 16, 2008, now Pat. No. 8,877,257.

(60) Provisional application No. 60/885,122, filed on Jan. 16, 2007.

(56) References Cited

U.S. PATENT DOCUMENTS

| | | |
|---|---|---|
| 2004/0062818 A1 | 1/2004 | Calderson |
| 2004/0137078 A1* | 7/2004 | Najafi ................ A01N 59/00 424/661 |
| 2004/0208940 A1* | 10/2004 | Selkon ................ A61K 33/00 424/661 |
| 2005/0139808 A1 | 6/2005 | Alimi |
| 2005/0142157 A1 | 6/2005 | Alimi |
| 2005/0196462 A1 | 9/2005 | Alimi |
| 2005/0221113 A1 | 10/2005 | Bitowft et al. |
| 2006/0235350 A1 | 10/2006 | Alimi et al. |
| 2006/0241546 A1 | 10/2006 | Alimi |
| 2006/0253060 A1 | 11/2006 | Alimi |
| 2007/0173755 A1 | 7/2007 | Alimi et al. |
| 2007/0196357 A1 | 8/2007 | Alimi et al. |
| 2007/0196434 A1 | 8/2007 | Alimi et al. |
| 2007/0231247 A1 | 10/2007 | Bromberg et al. |
| 2007/0292488 A1 | 12/2007 | Bassiri et al. |
| 2007/0292489 A1 | 12/2007 | Bassiri et al. |
| 2008/0279963 A1 | 11/2008 | Najafi et al. |
| 2009/0092685 A1 | 4/2009 | Selkon |
| 2009/0221989 A1 | 9/2009 | Najafi et al. |
| 2009/0258841 A1 | 10/2009 | Murphy et al. |
| 2009/0305267 A1 | 12/2009 | Krause et al. |
| 2010/0092399 A1 | 4/2010 | Alimi et al. |
| 2010/0106079 A1 | 4/2010 | Alimi |
| 2010/0112092 A1 | 5/2010 | Northey |
| 2010/0166809 A1 | 7/2010 | Northey et al. |
| 2011/0020474 A1 | 1/2011 | Najafi et al. |
| 2012/0164235 A1 | 6/2012 | Northey |
| 2012/0207853 A1 | 8/2012 | Alimi et al. |
| 2012/0237616 A1 | 9/2012 | Panicheva et al. |
| 2012/0251631 A1 | 10/2012 | Alimi et al. |
| 2014/0134277 A1 | 5/2014 | Panicheva et al. |
| 2015/0231173 A1 | 8/2015 | Sampson et al. |

OTHER PUBLICATIONS

Bickford, Larry, The Home EyeCare First Aid Kit, 1995, The EyeCare Connection, pp. 1-5.

Christensen, Eric, Gf and an Overview of OxcideTM: The Definitive Solution to Disinfection in Facility Water Distribution Systems & Equipment, 2003, pp. 1-17.

MSDS Oxcide, Oxcide, 2005, 2 pages.

Washington Publishers, Poison Ivy, Washington Publishers, 2005, pp. 1-5.

Women's Heathcare Topics, Stuffy Nose During Pregnancy, 2006, pp. 1-4.

Database Derwent on West (USPTO), London: Derwent Publications Ltd., AN 1998-537385, JP 10236961 A (Nobel Igaku Kenkyusho YG), abstract.

Sivaraj et al, "Ocular Manifestations of Systemic Lupus Erythematosus", 2007, Rheumatology, 46, pp. 1757-1762.

DryEyePain, Standard Treatments, DryEyePain.com, 2005, pp. 1-7, rittp:/fwww.dryeyepain.com/StandardTreatments.htm.

Marcinkiewicz et al., "Taurine and inflammatory diseases", Amino Acids, 2014, 46(1):7-20.

Augustin AJ, et al., (1995) Oxidative reactions in the tear fluid of patients suffering from dry eyes, Graefe's Arch Clin. Exp. Ophthalmol 233:694-698.

Wakamatsu et al., Tearful relations: oxidative stress, inflammation and eye diseases. Arq. Bras Oftalmol. 2008;71 (6 Supl):72-79.

Wang et al., Hypochlorous acis as a potential wound care agent; J_ Burns and Wounds, vol. 6, pp. 65-79, 2007.

* cited by examiner

METHODS AND COMPOSITIONS FOR TREATING INFLAMMATORY DISORDERS

PRIORITY

This application is a continuation-in-part of application Ser. No. 14/494,261 filed Sep. 23, 2014, which is a continuation of application Ser. No. 12/523,507 (now U.S. Pat. No. 8,877,257), which is a national stage of PCT/US2008/051208 filed Jan. 16, 2008, and which claims the benefit of U.S. 60/885,122 filed Jan. 16, 2007, each of which is hereby incorporated by reference in its entirety.

FIELD OF THE INVENTION

The present invention relates to compositions and methods for treating, preventing, or managing conditions characterized by infection and/or inflammation by administering hypohalous acid to the affected or susceptible areas.

BACKGROUND OF THE INVENTION

Many health conditions are characterized by inflammation, whether from microbial infection, sterile insult, or both. Inflammatory conditions, regardless of origin, share similar symptoms such as pain, heat, redness, fever, rash or joint swelling, and lesions, including wounds and ulcers to the skin, among others. While often difficult to discern underlying causes in a particular case, pain is often a key indicator of inflammation, because the swelling of the affected area/organ is pushing against sensitive nerve endings which then send pain and/or itch signals to the brain.

Conditions involving inflammation may be treated with, for example, topical or systemic antibiotics, antivirals, and/or anti-inflammatory agents depending on the suspected etiology. Such treatments are however limited by age restrictions, microbial resistance, drug toxicity, irritation, hypersensitivity and/or other side effects that may occur or develop especially with chronic use.

For example, in one model of inflammation, inflammation is initiated by either pathogen-associated molecular patterns (or PAMPs) or damage (or danger)-associated molecular patterns (DAMPs). PAMPs are molecules associated with pathogens that are recognized by cells of the innate immune system. These molecules are recognized by Toll-like receptors (TLRs) and other pattern recognition receptors (PRRs), and activate innate immune responses to protect the host from infection. DAMPs are molecules that can initiate and perpetuate a noninfectious inflammatory response, and are often cytosolic or nuclear components that are released from the cell, for example upon cell necrosis. Innate immune responses activated by PAMPs and DAMPs include inflammatory responses or inflammatory processes/cascades such as the inflammasome, which further include itch and pain mediators and their respective receptors, prurireceptors and nociceptors in the skin nerve terminal. Certain mediators of the inflammatory cascade are the same, whether initiated by PAMPs or DAMPs, and can include, α-2 macroglobulins, TNF-α, IL-2, IL-6, Il-1β, IL-8, TSLP, IL-4, IL-13, IL-17, IL-18, IL-31, among others.

It is an object of the invention to provide a broadly effective and safe treatment for conditions characterized by inflammation, whether originating from microbial or sterile insult, and such conditions include acute and chronic inflammation, as well as delayed-type and immediate-type hypersensitivity. It is also an object of the invention to provide a broadly effective and safe treatment for the prevention of diseases and conditions associated with or caused by prolonged or untreated inflammation. It is an object of this invention to provide compositions and methods that are safe and effective for prolonged and/or prophylactic use, by patients of all ages including pediatric and geriatric patients, and/or immunocompromised patients, for the prevention and management of inflammation.

SUMMARY OF THE INVENTION

In one aspect, the present invention provides a method for treating, preventing, or managing a condition involving infection and/or inflammation, including acute and chronic inflammation, as well as delayed-type and immediate-type hypersensitivity. Thus, the invention in various embodiments provides methods for treating or preventing microbial infection and the associated inflammatory response, as well methods for treating or preventing inflammatory conditions that lead to or are susceptible to secondary microbial infection. Further, in various embodiments, the invention provides methods for treating inflammation, such as chronic inflammation, without any associated microbial infection.

In particular embodiments, the invention provides methods for treating patients having hypersensitivity conditions in the presence or absence of microbial infection. In various embodiments the method comprises administering a hypochlorous acid solution to the affected area, wherein the hypochlorous acid solution has 20-5000 ppm (e.g., 20-about 1000 ppm) of available free chlorine and is at least 90% hypochlorous acid relative to the total concentration of hypochlorous acid, hypoclorite, and $Cl_2$ (molecular chlorine). In various embodiments, the condition is characterized by Type I hypersensitivity, Type II hypersensitivity, Type III hypersensitivity, and/or Type IV hypersensitivity. The invention in various embodiments inhibits and reduces inflammatory symptoms, and prevents "flare-ups" of an underlying chronic inflammatory condition. The invention in various embodiments can be used to prevent diseases or conditions caused by prolonged and/or untreated inflammation.

In various embodiments, the invention provides for administering the hypochlorous acid solution or composition to one or more affected regions, via enteral (oral, gastric and rectal), parenteral (intravenous, intra-arterial, intraosseous, intra-muscular, intrathecal, sub-cutaneous) or other (sublingually, buccally, rectally, vaginally, intra-articular, by the ocuIuar or otic route, nasally, cutaneously for topical or systemic effect, by inhalation or nebulization, or transdermally) or as an irrigant to one or more tissues or organs (e.g., during surgery or after trauma). For example, in various embodiments, the affected region is one or more of the eyes, ears, nose, sinus, throat, mouth (e.g., gingiva), or skin. In other embodiments, the affected region is one or more of the intestinal tract and/or colon, lungs, urogenital system (urinary tract or vagina), skeletal muscle, ligaments, tendons, joints, bones, peritoneum, kidney, liver, pancreas, or vasculature.

In certain embodiments, the condition includes an ocular condition, such as those affecting the conjunctiva, uvea, eye lids, oil glands, and lacrimal ducts, such as: bacterial, viral, or allergic conjunctivitis, uveitis, blepharitis, external and internal hordeolum, canaliculitis, dacrocystitis, and chalazions. Such conditions also include various conditions affecting the ear (including the inner ear, middle ear, ear canal, and ear drum), nose, mouth and throat, including rhinitis, sinusitis, rhinorrhea, otitis media, external otitis, myringitis, pharyngitis, and stomatitis.

The invention provides a broadly effective method for cleansing and treating the inflamed and/or infected regions, and in a manner relatively independent of the etiology of the inflammation or infection, and in a manner that avoids toxicity, hypersensitivity, and other side effects of conventional agents. The method of the invention is useful as an alternative or adjunct therapy to conventional antibiotics, antivirals, decongestants, antihistamines, immunosuppressants/immunomodulators, analgesics/anesthetics and steroid treatments, or as an alternative to therapy using a combination of conventional medicaments.

The methods of the invention are particularly suitable for prolonged and/or prophylactic use, because of the associated age restrictions, side effects, and/or drug resistance issues with alternative therapies. The methods are further suitable for individuals prone to such infections and/or inflammatory conditions, or individuals that typically experience hypersensitivity or severe side effects with other treatments.

DETAILED DESCRIPTION OF THE INVENTION

Figure 1:
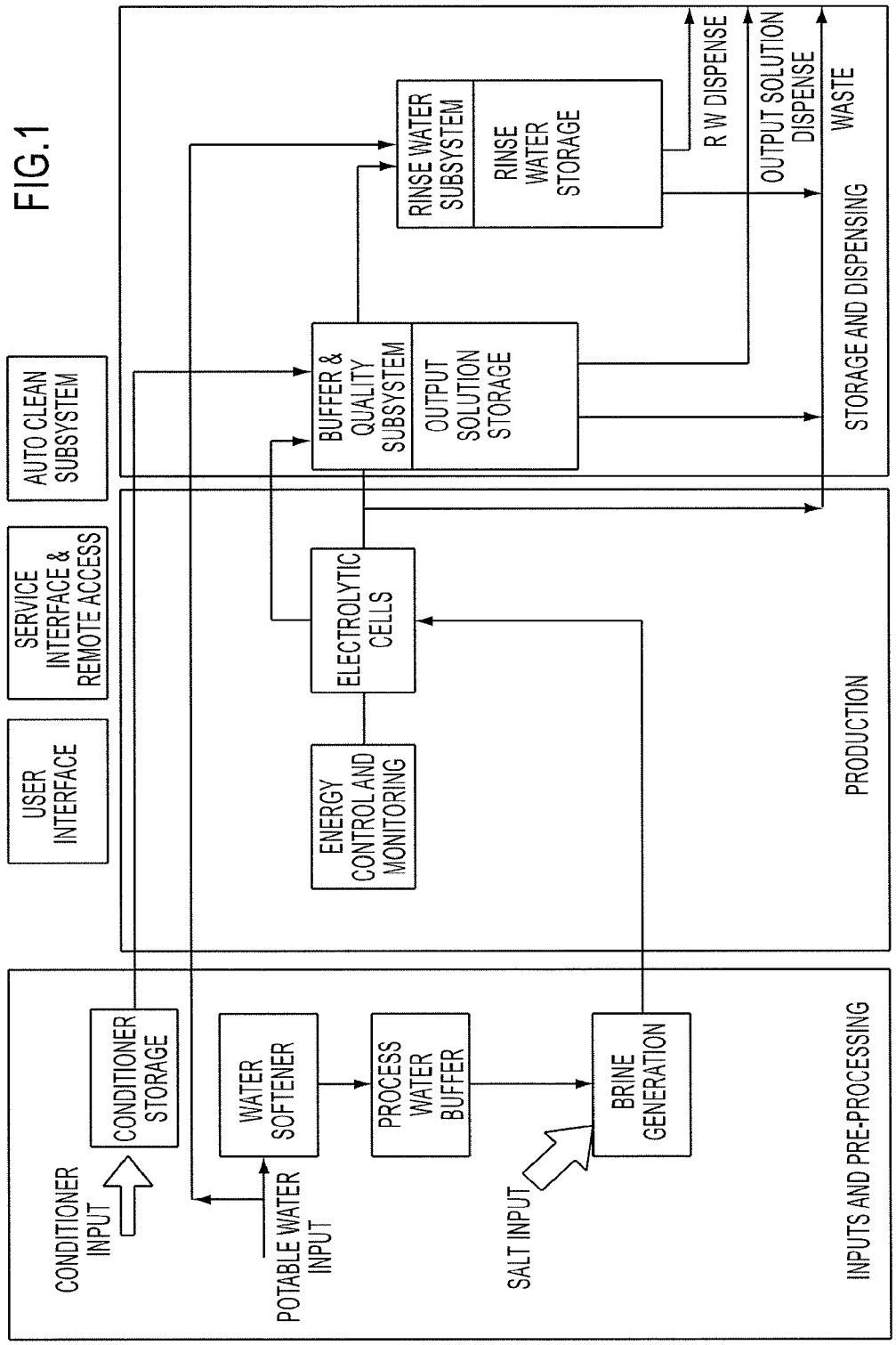
FIG. 1 is a schematic outline of the main processing stages for producing an electrolyzed saline solution in accordance with certain embodiments of the present invention.

The present invention provides compositions and methods for treating, preventing, or managing a condition characterized by infection and/or inflammation, by administering a hypohalous acid, such as HOCl, to the affected area.

Hypochlorous acid (HOCl) is an oxidant and antimicrobial that is produced by the human body's natural immune system. HOCl is generated as the final step of the Oxidative Burst Pathway, with large quantities of HOCl being released into phagocytic vesicles to destroy invading microorganisms. It is considered, without wishing to be bound by any theory, that hypochlorous acid exerts an antimicrobial effect by attacking the surface and plasma membrane proteins, impairing transport of solutes and the salt balance of bacterial cells (Pieterson et al, Water S A, 22(1): 43-48 (1996)). As described herein, it is also considered that HOCl exhibits previously unrecognized anti-inflammatory properties. This unique combination of anti-microbial and anti-inflammatory properties makes HOCl a promising therapeutic candidate for a variety of ailments.

In accordance with the present invention, exogenous hypohalous acid is administered for treating or preventing conditions characterized by infection and/or inflammation. The compositions of the invention are non-irritating and non-sensitizing to the skin, non-irritating to the eyes, not harmful if swallowed, show no evidence of mutagenic activity, and are safe for routine, prolonged, or prophylactic use. An added advantage is that there is no resistance or tolerance developed by the microorganisms, as occurs with the use of conventional antibiotics, and there is generally no hypersensitivity as occurs with some agents conventionally administered to treat microbial infections and inflammatory conditions. Further still, hypochlorous acid does not result in the panoply of side effects observed for conventional agents.

Conventional agents often result in a large range of potential undesirable side effects that are not observed with HOCl treatment. For example, antibiotics can induce rash, diarrhea, abdominal pain, nausea/vomiting, drug fever, hypersensitivity (allergic) reactions, serum sickness, vaginal candidiasis, and photosensitivity. Common anti-virals are reported to induce nausea, vomiting, diarrhea and headache, as well as agitation, confusion, rash, anemia, muscle pain, hypersensitivity reactions, seizures, and hepatitis. Antihistamines and decongestants are known to induce drowsiness, dizziness, dry mouth/nose/throat, headache, upset stomach, constipation, and trouble sleeping. Immunosuppressants/immunomodulators are reported to induce headache, nausea, vomiting, diarrhea, and malaise, as well as decreased kidney function, hepatitis, increased risk of infections, diabetes, increased cholesterol levels, sleep problems, mild tremor, high blood pressure, swollen gums, tingling of the fingers and feet, increased facial hair, and increased risk of lymphoma. Analgesics and anesthetics, such as opioids, have shown common side effects that include sedation, dizziness, nausea, vomiting, constipation, physical dependence, tolerance, and respiratory depression. Common side effects of local anesthetics include flushing or redness of the skin, itching skin, small red or purple spots on the skin, and unusually warm skin. Steroids are reported to induce increased appetite, weight gain, sudden mood swings, muscle weakness, blurred vision, increased growth of body hair, easy bruising, lower resistance to infection, swollen, puffy face, acne, osteoporosis, worsening of diabetes, high blood pressure, stomach irritation, nervousness, restlessness, difficulty sleeping, cataracts or glaucoma and water retention or swelling. By providing HOCl as an alternative therapy, side effects of conventional agents can be avoided.

The hypohalous acid solution may be generated by electrolysis of salt, such as saline (NaCl), and may contain a mixture of oxidizing species, but the oxidizing species are predominantly hypochlorous acid (HOCl). Hypochlorous acid and hypochlorite are in equilibrium and the position of the equilibrium is determined solely by the pH, which may be controlled by the electrochemical generator. The hypohalous acid solution may have a pH of from about 4 to about 7, but in certain embodiments has a pH of from about 5 to about 7, or from about 5.0 to about 6.5, or from about 5.4 to about 5.8. For example, the hypohalous acid solution may have a pH of about 5.4. The pH of the solution can be controlled, for example, by modulating the chemical properties of the solution, or (where an electrolyzed solution is used as the source of hypohalous acid) the hydraulic regime within the electrochemical cell system, the applied electric current, as well as salinity and composition of the feed solution, or the recirculation of the catholyte produced by the electrochemical cell.

In certain embodiments, the electrolyzed solution consists of essentially hypohalous acid as the active agent (e.g., HOCl), but in certain other embodiments may contain, or may also contain, other oxidizing or radical producing species such as a hypohalite (e.g., hypochlorite), hydroxide, $H_2O_2$ and $O_3$. These species may provide additional anti-microbial or anti-inflammatory activity, and may have additional benefits for clearing bacterial debris, biofilm, or discharge, such as where the hypohalous acid solution is used for treating ear infections, bacterial conjunctivitis or for cleaning or storing contact lenses. In certain embodiments, the hypohalous acid (e.g., HOCl) solution contains at least 80% hypohalous acid relative to the total concentration of hypohalous acid, hypohalite, and molecular halogen (Cl$_2$) (as 100%). The hypohalous acid may have, however, at least 90%, at least 95%, or at least 98% hypohalous acid relative to the total concentration of hypohalous acid, hypohalite, and molecular halogen (Cl$_2$) (as 100%). Such embodiments may allow for higher levels of active chlorine to be administered, while avoiding any irritation as a result of the solution. Hypochlorite has been known for quite some time to have toxic properties on mammalian cells due to high pH in addition to required concentration of available chlorine, and thus may not be desirable for long term use or may not have a sufficient therapeutic window for some anti-inflammatory applications. Thus, in some embodiments, the level of hypochlorite in the solution or composition is limited (e.g., about 10% or less, about 5% or less, or about 3% or less relative to the total concentration of hypochlorous acid, hypochlorite, and molecular halogen (Cl$_2$) (as 100%).

The hypohalous acid solution, such as an HOCl solution, contains available free chlorine (AFC) at from about 5 to about 5000 parts per million (ppm), or from about 5 to about 1000 ppm in some embodiments. In some embodiments, the solution has an AFC content of less than about 250 parts per million. For example, the solution may have an AFC content of from about 20 to about 200 ppm, such as from about 100 to about 200 ppm, or of from about 50 to about 100 ppm, or from about 20 to about 50 ppm. Such solutions may be particularly suited for routine, prolonged, and/or prophylactic care, including routine cleansing and hygiene. In certain other embodiments, the solution has an AFC content of greater than about 250 ppm. For example, the solution may have an AFC content of from about 250 to about 600 ppm, or from about 250 to about 400 ppm, or from about 400 to about 500 ppm, or from about 500 to about 600 ppm. In some embodiments, the HOCl is formulated at an AFC of from about 250 ppm to about 5000 ppm, such as from about 400 ppm to about 2000 ppm, or from about 500 ppm to about 1500 ppm, or from about 1000 to about 1500 ppm. Such solutions are potent biocides, and can help reduce and control inflammation, including immediate-type hypersensitivity reactions, such solutions are not generally irritating to the skin, eye, nasal mucosa, and ear, and are not harmful to contact lenses.

Thus, in various embodiments, the invention provides a method for treating a patient having an inflammatory or hypersensitivity condition in the presence or absence of microbial infection, where the method comprises administering a hypochlorous acid formulation to the affected area. The hypochlorous acid formulation has from about 20 to 5000 ppm AFC, and in some embodiments, has about 20 to 1000 ppm AFC. The formulation in various embodiments is at least 90% hypochlorous acid relative to the total concentration of hypochlorous acid, hypochlorite, and molecular chlorine. The hypochlorous acid solution may be prepared by electrolysis of a chloride salt.

As used herein, the term "affected area" is any tissue, organ, or part of the body in which symptoms of the inflammatory condition manifest, and which may include the skin, mucus membranes, eyes, ears, nose, sinus cavity, throat, mouth (e.g., gingiva), lungs, connective tissue (including skeletal muscles, ligaments, tendons, joints), nervous system (including activation or inhibition of nerve-based signaling responses such as scratching/itching or pain), intestinal tract (e.g., colon), urogenital system (including urinary tract or vagina), as well as systemic inflammation affecting the vasculature, or in some embodiments the peritoneum or one or more organs such as the kidney, liver, or pancreas. The affected region in any given embodiment will determine the route of administration, which will range from via enteral (oral, gastric and rectal), parenteral (intravenous, intra-arterial, intraosseous, intra-muscular, intrathecal, sub-cutaneous) or other (sublingually, buccally, rectally, vaginally, intra-articular, by the ocluuar or otic route, nasally, cutaneously for topical or systemic effect, by inhalation or nebulization, or transdermally) or as an irrigant to one or more tissues or organs (e.g., during surgery or trauma).

As used herein, the term "treating" refers to providing therapy to a patient to prevent (by means of prophylactic treatment), reduce, inhibit, ameliorate, or manage symptoms (e.g., inflammatory symptoms) of a disease, or to slow or stop progression of the disease, as well as in some embodiments, to prevent onset or re-occurrence of a condition or symptom. For example, in various embodiments the invention provides methods of treating tissues to inhibit, reduce, or prevent inflammatory processes including acute, chronic, and delayed reactions, thereby allowing regeneration and/or healing of tissues, and/or preventing tissue damage or loss of tissue integrity.

As used herein, the term "prolonged use" refers to treatment of a chronic condition. Generally, a chronic condition is a condition that will not be eliminated even with therapy, and thus the therapy is intended to reduce, inhibit, or prevent (e.g., by means of prophylactic treatment) inflammatory symptoms, thereby managing the condition. Prolonged use generally includes treatment for at least about six months, at least about one year, at least about two years, or more.

The electrolyzed solution of the invention may also contain from about 0.1 to 2.0% w/v salt, such as NaCl. In some embodiments, the invention contains 0.4 to 1.5% w/v salt, or may be a normal saline solution (0.9% w/v NaCl). In some embodiments, the solution is isotonic with physiological fluids, such blood, saliva or tears. In some embodiments, the solution is hypotonic with physiological fluids. While the hypohalous solution may be administered at room temperature, the solution may alternatively be heated, for example, to body temperature or about body temperature, or above body temperature to help drain fluids from the site of infection as well as loosen oils that spawn infection. In certain embodiments, the hypohalous acid is administered at below body temperature. Such embodiments may be particularly suited to control acute inflammation.

The hypohalous acid may be prepared by electrolysis of one or more halide salts, including Cl, Br, and I. Thus, the hypohalous acid may include one or a mixture of HOCl, HOBr, HOI. In certain embodiments, the electrolyzed solution is generated using a mixture of physiologically balanced salts, as disclosed in U.S. Pat. No. 6,426,066, which is hereby incorporated by reference in its entirety. Such salts may include sodium halides (e.g., NaCl), potassium halides (e.g., KCl) and magnesium halides (e.g., MgCl$_2$).

The composition may be formulated as a liquid, such as an eye drop, eye wash, wash for contact lenses, gargle, oral rinse, nasal rinse or throat spray, or ear drop. In still other embodiments, the composition may take the form of a paste, cream, emulsion, gel, and/or foam for application to the skin or dentia. Such formulations may be prepared using conventional additives known in the art and/or as described herein. In embodiments employing pastes, creams, emulsions, gels, and/or foams, the solution is better contained around the site of infection or inflammation by limiting run-off. Convenient applicators for creams, foams, and the like are known, and may be used in accordance with the present invention. Alternatively still, the composition may be formulated so as to be delivered by aerosol, mist, or steam, impregnated into wound dressings, adhesive, or dissolving strips, patches, suppositories, or encapsulated in silicon or other carriers, as nanoparticles or free-standing in liquids, suspensions, powders, pills or capsules for the purposes of release, targeted release or extended-release via enteral or parenteral administration.

Further still, the composition in various embodiments can be administered systemically, for example, by aerosol to the lungs or by intravenous or subcutaneous delivery of particles that encapsulate and release HOCl in the circulation, either in a sustained manner or targeted to particular tissues or organs. In some embodiments, the solution or composition is formulated for colonic, vaginal, urinary tract, or peritoneal irrigation, or is formulated for injection into joint spaces. In some embodiments, the solution or composition is formulated for irrigation of tissues or organs during or following surgery to prevent or reduce inflammatory complications, such as those that may occur post-surgery. In some embodiments, the composition is formulated for treating donor tissue or organs (e.g., kidney, liver, lung, heart, skin, and cornea) prior to or during transplantation.

The electrolyzed solution may have an oxidation reduction potential (redox) of greater than about +650 mV, greater than about +950 mV, such as about +1000 mV. A high redox potential allows for the quick and efficient destruction of microbes (bacteria, viruses, fungi and spores) that may infect or colonize the affected region or surrounding tissues. In certain embodiments of the invention, the hypohalous acid solution has an antimicrobial rate (D Value) of 1 log reduction of *Bacillus subtilis* or *Clostridium difficile* spores in less than 15 seconds with a 9:1 electrolyzed solution: innoculum mix. In some embodiments, the solution has an antimicrobial rate as low as 3.4 seconds. Generally, the hypohalous acid is effective on a broad spectrum of bacterial, fungal, and viral pathogens.

In certain embodiments of the present invention, the hypohalous acid is formulated or administered in combination with another therapeutic or cleansing agent. Non-limiting examples of therapeutic agents include anti-microbial agents such as antibiotics, antivirals, anti-fungal and anti-parasitics, immune-modulators/suppressants anti-inflammatory agents, anti-histamines, analgesics, local anesthetics, anti-oxidants such as vitamins, and moisturizing agents. For example, the hypohalous acid may be formulated or administered with antibiotics such as bacitracin, neomycin, neosporin, framycetin, fusidic acid, corticosteroid, chloramphenicol, gentamicin, tobramycin, ceftriaxone, sulfacetamide, erythromycin, gentamicin, ciprofloxacin, ofloxacin, cefoxitin, cefotaxime, spectinomycin, tetracycline, doxycycline, and azithromycin; anti-virals such as acyclovir, valacyclovir, famciclovir, and oseltamivir; anti-fungals such a as ketoconazole, fluconazole, itraconazole, voriconazole, terbinafine, and nystatin; anti-parasitics such as metronidazole, ivermectin, pyrantel pamoate, albendazole, and atovaquone-proguanil immune-modulators/suppressants such as thalidomide, lenalidomide, apremilast, cyclosporine, prednisone and tacrolimus; corticosteroids and NSAIDs such as aspirin, ibuprofen, naproxen sodium, celecoxib; anti-histamines such as diphenhydramine, loratadine, fexofenadine, cimetidine, ranitidine, ciproxifan, and cromoglycate; analgesics such as acetaminophen/paracetamol, buprenorphine, codeine, meperidine, and tramadol; local anesthetics such as epinephrine, lidocaine, bupivacaine, and benzocaine; anti-oxidants such as vitamin A & E; moisturizing agents such as silicones, emollients, lanolin, mineral oil, urea, alpha-hydroxy acids, glycerine, fatty acids, ceramides, collagen or keratin. Non-limiting examples of cleansing agents include alcohol, betaine, mild soap solutions, bicarbonate or saline solutions, or electrolyzed solutions including catholytes.

The composition may comprise a pharmaceutically acceptable carrier. Non-limiting examples of suitable carriers include hectorite, bentonite, laponite, oil emulsions, polyvinyl alcohol, povidone, hydroxypropyl methyl cellulose, poloxamers, carboxymethyl cellulose, hydroxyethyl cellulose, and purified water. The composition may also include various other ingredients, such as tonicity agents, buffers, surfactants, co-solvents, viscosity building agents, preservatives, and other therapeutic agents.

Regarding tonicity agents, such agents may be employed to adjust the tonicity of a composition, for example, in the case of an ophthalmic composition, to the tonicity of natural tears. For example, sodium chloride, potassium chloride, magnesium chloride, calcium chloride, dextrose and/or mannitol may be added to the composition to approximate physiological tonicity. Such an amount of tonicity agent will vary, depending on the particular agent to be added and the type of composition. In general, however, the compositions will have a tonicity agent in an amount sufficient to cause the final composition to have an acceptable osmolality. For example, for an ophthalmic composition, the composition is generally in the range of about 150 to 450 mOsm, preferably 250 to 350 mOsm.

Regarding buffers, an appropriate buffer system (such as, for example, sodium phosphates, potassium phosphates, potassium carbonate, sodium bicarbonate, sodium borate or boric acid) may be added to the compositions to prevent pH drift under storage conditions. The particular concentration will vary, depending on the agent employed. Preferably, however, the buffer will be chosen to maintain a target pH within the range of pH 4-7 or a range as described herein.

Regarding a surfactant, various surfactants useful in conventional formulations may be employed. Exemplary surfactants include CREMOPHOR EL, lauramine oxide, myristyl dimethylamine oxide, polyoxyl 20 ceto stearyl ether, polyoxyl 40 hydrogenated castor oil, polyoxyl 23 lauryl ether and poloxamer 407.

Regarding viscosity building agents, such agents may be added to compositions of the present invention to increase the viscosity of the carrier. Examples of viscosity enhancing agents include, but are not limited to: synthetic silicates, polysaccharides, such as hyaluronic acid and its salts, chondroitin sulfate and its salts, dextrans, various polymers of the cellulose family; vinyl polymers; and acrylic acid polymers. For example, the composition may exhibit a viscosity of 1 to 400,000 centipoises ("cps").

Regarding preservatives, no additional antimicrobial agent is required, since the HOCl will function as a preservative; however, in some embodiments HOCl is combined with a second preservative or antimicrobial agent such as silver. In various embodiments, the HOCl is manufactured as sterile. The composition can also include other therapeutic agents such as anti-inflammatory agents, antihistamines, decongestants, antibiotics, analgesics, immune-modulators and suppressants and/or moisturizing agents known in the art.

In various embodiments, the inflammatory condition treated in accordance with the various embodiments is characterized by type I hypersensitivity, type II hypersensitivity, type III hypersensitivity, and/or type IV hypersensitivity. The inflammatory condition may be acute or chronic, and may be of allergic origin.

Type I hypersensitivity or (immediate-type hypersensitivity) is an allergic reaction provoked by re-exposure to an antigen (e.g., allergen). In type I hypersensitivity, an antigen is presented to CD4+ Th2 cells specific to the antigen that stimulate B-cell production of IgE antibodies also specific to the antigen. During sensitization, the IgE antibodies bind to receptors on the surface of tissue mast cells and blood basophils. Later exposure to the same allergen cross-links the bound IgE on sensitized cells, resulting in degranulation and the secretion of pharmacologically active mediators such as histamine, leukotriene (LTC4 and LTD4), and prostaglandin that act on the surrounding tissues. The principal effects of these products are vasodilation and smooth-muscle contraction. Exemplary Type I conditions for which the invention can be effective include allergic asthma, allergic conjunctivitis, allergic rhinitis, anaphylaxis, angioedema, urticaria, eosinophilia, drug allergy (e.g., penicillin, cephalosporin), or food allergy. Type I hypersensitivity can be further classified into an immediate and late-phase reaction. The immediate hypersensitivity reaction occurs minutes after exposure and includes release of vasoactive amines and lipid mediators, whereas the late-phase reaction occurs 2 to 4 hours after exposure and includes the release of cytokines.

In type II hypersensitivity (or cytotoxic hypersensitivity) the antibodies produced by an immune response bind to antigens on the patient's own cell surfaces. The antigens recognized may be self-antigens or extrinsic antigens that are adsorbed onto the cells during exposure to some foreign antigen. These cells are recognized by macrophages or dendritic cells, which act as antigen-presenting cells. This causes a B cell response, wherein antibodies are produced against the foreign antigen. Examples of type II hypersensitivity include Haemolytic Anaemia, Myasthenia Gravis, Grave's Disease, and Goodpasture's syndrome. Another form of type II hypersensitivity is called antibody-dependent cell-mediated cytotoxicity (ADCC). Here, cells exhibiting the foreign antigen are tagged with antibodies (IgG or IgM). These tagged cells are then recognized by natural killer cells (NK) and macrophages which in turn kill these tagged cells.

Type III hypersensitivity occurs when antigen-antibody complexes that are not adequately cleared by innate immune cells accumulate, giving rise to an inflammatory response and attraction of leukocytes. Type III hypersensitivity occurs when there is an excess of antigen, leading to small immune complexes being formed that do not fix complement and are not cleared from the circulation. Large complexes can be cleared by macrophages but macrophages have difficulty in the disposal of small immune complexes. These immune complexes insert themselves into small blood vessels, joints, and glomeruli, causing symptoms. Unlike the free variant, a small immune complex bound to sites of deposition (like blood vessel walls) are far more capable of interacting with complement. Such depositions in tissues often induce an inflammatory response, and can cause damage wherever they precipitate. The damage can result from the action of cleaved complement anaphylotoxins C3a and C5a, which, respectively, mediate the induction of granule release from mast cells, and recruitment of inflammatory cells into the tissue. Skin response to type III hypersensitivity is referred to as an arthus reaction, and is characterized by local erythema and some induration. Other examples of type III hypersensitivity include Systemic lupus erythematosus (SLE) (which can involve, for example, nephritis, skin lesions, and arthritis); glomerulonephritis, systemic vasculitis, arthritis, cutaneous vasculitis, Farmer's lung (which manifests as alveolar inflammation).

Type IV hypersensitivity is often called delayed-type hypersensitivity as the reaction takes two to three days to develop. Unlike the other types, it is not antibody mediated but rather is a type of cell-mediated response. CD4+ helper T cells recognize antigen in a complex with Class II major histocompatibility complex. The antigen-presenting cells in this case are macrophages that secrete IL-12, which stimulates the proliferation of further CD4+Th1 cells. CD4+ T cells secrete IL-2 and interferon gamma, further inducing the release of other Th1 cytokines, thus mediating the immune response. Activated CD8+ T cells destroy target cells on contact, whereas activated macrophages produce hydrolytic enzymes and, on presentation with certain intracellular pathogens, transform into multinucleated giant cells.

Examples of type IV hypersensitivity include the following. Diabetes mellitus type 1 affects pancreatic beta cells, leading to beta cell destruction and/or insulitis. Multiple sclerosis results from an attack on oligodendrocyte proteins, and resulting in demyelinating disease, perivascular inflammation, paralysis, and/or ocular lesions. Rheumatoid arthritis (RA) results from an attack on antigen in synovial membrane, and leading to chronic arthritis. RA often leads to the destruction of articular cartilage and bone (which can also involve type III hypersensitivity). Peripheral neuropathy which can result from attack on schwann cell antigen, leading to neuritis or paralysis. Hashimoto's Thyroiditis results from attack on thyroglobulin antigen, leads to hypothyroidism, goiter, and/or follicular thymitis. Crohn's disease involves inflammation of the ileum and colon. Allergic contact dermatitis results from contact with environmental chemicals including poison ivy and nickel, and manifests as itching and can include exposure to radiation, whether by exposure to artificial or natural UV in the course of living (leading to UV-damaged/aged skin), and/or exposure to radiation for the purposes of cancer treatment or for interventional procedures. Other examples include celiac disease, graft-versus-host disease, and chronic transplant rejection.

Whether the inflammation results from type I, II, III, or IV hypersensitivity responses, the inflammasome including certain pro-inflammatory cytokines (e.g., IL-1β, IL-2, IL-4, IL-6, IL-8, IL-18, and TNF-α, as well as other soluble or cellular factors such as α-2 macroglobulin and NF-kβ), and/or the inflammasome will be involved in the inflammatory response.

In various embodiments, the HOCl composition is applied to prevent diseases or conditions caused by prolonged and/or untreated inflammation. Examples of these diseases or conditions include: cancer (e.g. bowel cancer, lung cancer, skin cancer, ovarian Cancer, breast cancer among others; cardiovascular disease; diabetes; and metabolic disease).

In various embodiments, the HOCl composition is applied to treat or prevent lesions caused by inflammatory conditions by inhibiting the inflammatory processes and/or by maintaining skin homeostatis or by stimulating cell (e.g., skin cell) proliferation to heal lesion wounds. Thus, in some embodiments, the patient has an inflammatory condition that manifests as skin or mucosa lesions, and the HOCl formulation protects intact skin (e.g., from developing lesions) and/or promotes closing of wounds once developed. In some embodiments, the patient may have a condition that predisposes the patient to skin lesions, and is characterized by microbial infection or burden, inflammation, itch, high pH, and compromised barrier. HOCl as described herein acts in a multi-modal fashion to inhibit various stages of the condition, including reduction of the microbial burden, normalizing the pH, reducing itch, while reducing inflammatory mediators.

In various embodiments, the invention provides for administering the hypochlorous acid solution or composition to one or more affected regions. For example, in various embodiments, the inflammatory condition involves as an affected region, one or more of the eyes, ears, nose, sinus, throat, mouth, gingiva, or skin. In other embodiments, the inflammatory condition may have as an affected region, one or more of the intestinal tract/colon, lungs, urogenital system (e.g., urinary tract, vagina), skeletal muscle, ligaments, tendons, joints, bones, kidney, liver, pancreas, or vasculature.

Various inflammatory conditions that may be treated in accordance with the invention include: conditions of the eye such as allergic conjunctivitis, blocked glands, chalazion, stye, red eye, dry eye disease, uveitis, inflammation after eye surgery, dry or wet age-related macular degeneration (AMD); conditions of the nose or sinus cavity such as rhinitis, rhinorrhea, sinusitis, nasal congestion; conditions of the mouth or throat such as stomatitis, xerostomia, gingivitis, or pharyngitis; and conditions of the skin such as keratitis, dermatitis, acne or psoriasis.

Additional inflammatory conditions to be treated in various embodiments, which can affect a particular target tissue, or affect multiple tissues, organs, or systems, are as follows. Exemplary conditions that affect the lungs include allergic asthma, occupational asthma, bronchitis, chronic obstructive pulmonary disease (COPD), idiopathic pulmonary fibrosis (IPF), cystic fibrosis, Goodpasture Syndrome, or Farmer's Lung. Exemplary conditions that affect the skin include contact dermatitis, acne, angioedema, urticaria, Systemic lupus erythematosus (SLE), psoriasis, sarcoidosis, rosacea, dermatitis herpetiformis, sun-burn, and cutaneous vasculitis. Exemplary conditions that affect the colon or intestinal tract include Crohn's disease, celiac disease, ulcerative colitis, and hemorrhoids. Exemplary conditions that affect the joints or bones include arthritis (e.g., rheumatoid arthritis or osteoarthritis), multifocal osteomyelitis, traumatic knee injury, SLE, and gout. Exemplary conditions that affect the kidneys include Goodpasture Syndrome, SLE, glomerulonephritis, and kidney stones. Other exemplary conditions involving inflammation of an organ, system, or systemic inflammation include eosinophilia, drug allergy, food allergy, hemolytic anemia, myasthenia gravis, systemic vasculitis, diabetes mellitus type 1 and 2, Hidradenitis suppurativa, multiple sclerosis (MS), myelitis, peripheral neuropathy, Parkinson's Disease, hepatitis, renal failure, pancreatitis, Hashimoto's Thyroiditis, adult onset Still's disease, systemic onset juvenile idiopathic arthritis (SJIA) Schnitzler syndrome, Behcet's disease, SAPHO syndrome, macrophage activation syndrome, Familial Mediterranean Fever (FMF), cryopyrin-associated periodic syndrome (CAPS), TNF receptor associated periodic syndrome (TRAPS), Hyper-IgD syndrome, periodic fever, aphthous stomatitis, pharyngitis and adenitis (PFAPA), deficiency of interleukin-1 (IL-1) receptor antagonist (DIRA), Giant cell arteritis, graft versus host disease, amyloidosis, recurrent pericarditis, and neuromyelitis optica, amylotrophic lateral sclerosis, myeloma, and chronic transplant rejection.

In some embodiments, the HOCl is applied to the skin, either to reduce or inhibit inflammation, or to prevent inflammation in a patient with an acute or chronic inflammatory condition. For example, the affected areas of the skin may be characterized by an alkaline pH as compared to normal healthy skin. In such embodiments, the weak—acidic pH of the hypochlorous acid helps bring the skin to a pH that is more conducive to healing and healthy regeneration. Further, in some embodiments, application to intact but inflamed skin promotes healthy skin regeneration and barrier integrity, by inhibiting or reducing the tissue-damaging inflammatory response, thereby allowing the cells (e.g., dermal fibroblasts and/or keratinocytes) to proliferate in a manner consistent with the healing process. Further still, HOCl is not cytotoxic to these cells at the levels applied. The healing environment is further aided by reducing the microbial burden of the inflamed tissue, where otherwise infection might spawn due to loss of barrier integrity. Thus, in various embodiments, the hypochlorous acid formulation results in one or more of a reduction of microbial burden, a reduction of inflammation, reduced pruritis, enhanced skin cell regeneration, and normalizes skin pH. In some embodiments, the patient has a condition characterized by microbial bioburden or infection, inflammation, itch, lesions, and high skin pH at the affected region. In some embodiments, the patient has a condition characterized by skin lesions, with or without active lesions. While the HOCl formulation promotes healing of active lesions and normalization of the skin, new lesions are prevented from forming.

In some embodiments involving symptoms of microbial infection, the hypohalous acid is administered after unsuccessful topical or systemic antibiotic treatment. For example, where the invention reoccurs or is generally unaffected by antibiotic treatment, hypohalous acid may be administered to the affected regions as discussed herein, without further investigation as to the causative agent where not practical. In still other embodiments, the hypohalous acid may be administered to the affected regions in place of antibiotic treatment, thus making antibiotic treatment unnecessary. For example, administering hypohalous acid in accordance with the present invention may be used as an alternative to administration of a beta-lactam or fluoroquinolone antibiotic, thereby avoiding the hypersensitivity reactions common with such drugs. This embodiment is particularly advantageous where antibiotic resistance has already been developed by the microorganism, the hypohalous acid being an alternative to potential "last lines of defense" with antibiotic treatment, since resistance will not be developed to the hypohalous acid, and no further resistance to conventional antibiotics will then be cultivated.

In certain embodiments, the invention is a superinfection, including both viral and bacterial etiology. In such embodiments, the hypohalous acid may be administered in place of other agents or combination therapies, to treat and or help clear the various microbial pathogens.

The hypohalous acid may also be used as an adjunct cleanser along with antibiotic or steroidal treatment to provide synergistic disinfecting and/or anti-inflammatory effects. For example, when used in conjunction with an antibiotic, the treatment provides a potent antimicrobial effect, while avoiding or limiting the development of antibiotic resistance. This aspect of the invention is particularly useful where the infection is chronic or recurring, since continued or repeated antibiotic treatment is generally not accepted.

The inflammatory condition may be present in a human or animal patient of any age (including pediatric and geriatric patients) as well as immunocompromised patients. Exemplary animal patients include mammals such as dogs, cats, horses, lamb, cattle, goats, pigs, and guinea pigs. The present invention further contemplates preventive care (including prophylactic use) for such inflammatory conditions or prevention of such conditions where the patient is genetically or environmentally pre-disposed to such conditions, as well as conditions that don't completely resolve with antimicrobial or steroidal treatment.

In certain embodiments, the present invention relates to treating an ocular condition, especially an ocular condition originating from an infection and/or inflammatory condition. The ocular condition may affect any portion of the eye or surrounding areas, such as the conjunctiva, uvea, eyelid, oil glands, and lacrimal ducts. Exemplary ocular conditions include: red eye; dry eye (including dry eye syndrome); conjunctivitis of bacterial, viral, or allergic origin; uveitis, blepharitis; external or internal hordeolum; canaliculitis; dacrocystitis; and chalazions.

The invention includes the treatment and prevention of ocular infections caused by a variety of pathogens, such as, for example, a bacterial agent, a viral agent, a parasitic agent, and/or a fungal agent. Non-limiting examples of bacterial agents include *Streptococcus* spp. (e.g. *pneumoniae*), *Staphylococcus* spp. (e.g., *aureus*), *Haemophilus* spp. (e.g., *influenzae*), *Pseudomonas* spp. (e.g., *aeuruginosa*), *Chlamydia* spp. (e.g., *trachomatis, psittaci, pecorum*), *Neisseria* spp. (e.g. *gonorrhoeae*), and *Actinomyces* species. Non-limiting examples of viral agents include adenovirus, respiratory syncytial virus (RSV), influenza (including parainfluenza), coxackie virus, rhinovirus, coronavirus, and herpes simplex virus. Non-limiting examples of fungal agents include *Candida* species, *Fusariu* species, and *Aspergillus* species. A non-limiting example of a parasitic agent is an eyeworm. Certain bacterial agents may be more common in certain patient subpopulations. For example, different strains of *Chlamydia psittaci* and *Chlamydia pecorum* cause significant eye infection in cats, lambs, goats, and guinea pigs. These infections are occasionally transmitted to humans. Further, eyeworms are common parasites of horses and cattle, goats, pigs, dogs and cats. Thus, in invention provides further provides additional benefits in the farming industry where antibiotics and other active agents should be used sparingly.

These microbial agents may be involved in various ocular infections including blepharitis; hordeola, such as external hordeolum and internal hordeolum; conjunctivitis, such as viral conjunctivitis or bacterial conjunctivitis, conjunctivitis in newborns (opthalmia neonatorum) due to *Chlamydia trachomatis* or *Neisseria gonorrhoeae*, chlamydial disease in adults such as inclusion conjunctivitis and trachoma, or gonococcal conjunctivitis in adults; iridocyclitis and panopthalmitis caused by *Bacillus subtilis*; lacrimal system infections such as canaliculitis and dacrocystitis; keratitis, such as viral keratitis (herpes simplex virus), bacterial keratitis and fungal keratitis (e.g., *Fusarium*), including among soft contact lens wearers; toxoplasmosis, including in dogs and cats; feline herpes virus, which is a common cause of eye and upper respiratory infections in cats; uveitis, including in large animals, such as cattle, caused by *Listeria*; and eye infections caused by avian flu or other eye conditions and infections secondary to other medical conditions.

In certain embodiments of the invention, the ocular condition involves a bacterial infection that is antibiotic resistant. For example, the bacterial infection may be resistant to antibiotics commonly employed to combat eye infections either topically or systemically, such as sulfacetamide, erythromycin, gentamicin, ciprofloxacin, ofloxacin, cefoxitin, ceftriaxone, cefotaxime, spectinomycin, tetracycline, doxycycline, azithromycin, or bacitracin. In these and other embodiments, the bacterial invention may be resistant to beta-lactam antibiotics or fluoroquinolones. For example, the infection may involve methicillin-resistant *Staphylococcus aureus* (MRSA), for which the present invention is effective.

In certain embodiments, the ocular condition involves a viral infection, which may further include a secondary bacterial infection, such that conventional antibiotic treatment is necessarily insufficient.

In certain embodiments, the ocular condition may be a bacterial infection that produces a discharge that hinders vision and/or eye function, such as bacterial conjunctivitis. In these embodiments, the invention provides the benefit of effectively cleaning sticky discharge, biofilm, or debris from the eye in a manner that reduces the risk of spreading the infection to an unaffected eye or another individual. Where the condition involves biofilm, the hypohalous acid deactivates the polymatrix material of the biofilm to facilitate removal (cleansing), and disinfection. Hypohalous acid contact with biofilm formation dissolves the protective polysaccharaide matrix of the biofilm aiding in the effective removal of pathogens and debris.

In certain embodiments, the ocular condition involves an inflammatory disorder or hypersensitivity reaction (including types I, II, III, and/or IV). For example, the ocular condition may involve an immediate-type hypersensitivity reaction such as allergic conjunctivitis. In other embodiments, the condition may result from a blocked gland or chronic inflammatory condition, including styes and chalazions, which may also develop an acute bacterial infection. Such conditions may be recurring or may be difficult to completely clear. Other inflammatory ocular conditions that may or may not involve microbial infection include uveitis.

In some embodiments, the subject has conjunctivitis, commonly known as pink eye. Conjunctivitis is an inflammation of the conjunctiva, the outer-most layer of the eye that covers the sclera. While many of the signs and symptoms of conjunctivitis are relatively non-specific, there are several etiologies that may be causative in a given case. The three most common causes of conjunctivitis are bacterial infection, viral infection, or an allergic reaction.

In some embodiments, the composition is applied to treat blepharitis, chalazion, or hordeola. Blepharitis is an inflammation of the eyelid margins, and is usually caused by an infection of *Staphylococcus aureus*. Blepharitis can lead to a chalazion, or lead to a stye (hordeolum). A chalzion is a cyst in the eyelid caused by inflammation of a blocked meibomian gland, usually on the upper eyelid. A chalazion may spawn bacterial infection. When the condition does not resolve on its own, a chalazion may be injected with corticosteroid or be surgically removed. Hordeola include both external hordeolum, or "stye", and internal hordeolum (acute meibomianitis). Styes are lesions at the base of the eyelashes and are predominantly caused by infection of *Staphylococcus aureus*.

In some embodiments, the composition is applied to treat infection and/or inflammation of the lacrimal system, such as canaliculitis and dacrocystitis. Canaliculitis can be caused by *Actinomyces* infection. Dacrocystitis is often due to streptococci or *Staphylococcus aureus*.

In certain embodiments, the ocular condition is prevention of infection and/or inflammation resulting from an eye surgery or trauma to the eye.

Treating an ocular condition in accordance with the present invention generally involves alleviating the cause or symptoms of the condition, and can include: reducing inflammation or hypersensitivity in the eye or surrounding area; reducing pain; reducing irritation in the eye or surrounding area; reducing redness in the eye; reducing discharge from the eye; improving vision from the eye; clearing a microbial infection; preventing, or reducing the spread of a microbial infection, including the spread of infection from the infected eye to an uninfected eye; and moisturizing or reducing dryness of the eye. These can be measured or determined by comparing the patient's condition prior to and after treatment with hypohalous acid in accordance with the present invention. Alternatively, treatment can be determined relative to a patient having the same or similar condition who has not been treated with the hypohalous acid in accordance with the present invention. In certain embodiments, the administration of hypohalous acid treats both an infection and inflammation, such as acute or chronic inflammation, associated with an ocular condition.

In certain other embodiments, the hypohalous acid is administered prophylactically, especially where eye infections are likely to occur or be transmitted among persons. Thus, in this embodiment, the invention involves administering the hypohalous acid before an infection and/or inflammation develops. Such prophylactic care might include routine cleaning of the eyes and surrounding areas, such as the eyelids, with the hypohalous acid, or routine rinsing of contact lenses by applying the hypohalous acid to the contact lenses to decontaminate and clear debris and biofilm. Such embodiments can result in the prevention of an ocular infection, can prevent the worsening of an existing ocular infection caused by contaminated lenses, or can prevent irritation of the eyes caused by bacterial biofilm. In other embodiments, the invention involves administering hypohalous acid to the environment via fogging, misting, or humidifying, to prevent the transfer of pathogens from air droplets into the eyes of susceptible individuals.

In certain embodiments, the ocular condition may be a bacterial infection that produces a discharge that hinders vision and/or eye function, such as bacterial conjunctivitis. In these embodiments, cleaning the eye and the surrounding areas with the hypohalous acid of the invention provides the benefit of effectively cleaning debris, biofilm, and/or discharge from the eye in a manner that reduces the risk of spreading the infection to an unaffected eye or another individual.

In certain embodiments, the ocular condition may result from an acute or chronic inflammatory condition, which may develop an acute infection. In these embodiments, the hypohalous acid is administered to treat both the infection and the underlying inflammation. Thus, the hypohalous acid may be administered instead of steroidal drops or systemic steroidal medications, or antibiotics, thereby avoiding the potential adverse reactions of such treatments. In certain other embodiments, the hypohalous acid is used to clean the region during the duration of steroidal and/or antibiotic treatment. In one embodiment, hypohalous acid is administered to the eye of a patient inflicted with uveitis, during the duration of steroid treatment. For example, the hypohalous acid may be used in conjunction with glucocorticoid steroids, either as topical eye drops (such as betamethasone, dexamethasone or prednisolone) or oral therapy with prednisolone tablets. Likewise, when the condition has an allergic origin, such as allergic conjunctivitis, the hypohalous acid may be used alongside an antihistamine to more effectively inhibit release of inflammatory mediators from mast cells.

In certain embodiments of the present invention, the hypohalous acid solution is administered with treatment using a warm compress, especially where the condition is blepharitis, an external hordeolum, an internal nordeolum, or a chalazion. In these embodiments, the hypohalous acid may be used for routine cleansing of the affected area for the duration of the treatment, and after treatment to avoid recurrence of the condition.

In certain embodiments, the hypohalous acid solution may be administered to two or more sites in the ocular system of a patient. For example, the hypohalous acid may be administered as drops to the eye or eye wash, and as a cleanser for the eye lids and/or eyelid margins.

In another embodiment, the hypohalous acid treatment is followed by treatment with an antioxidant, such as a vitamin.

The hypohalous acid and compositions of the present invention may be administered in any appropriate dosage form such as a liquid, aerosol, gas, or semi-solid including a solution, suspension, viscous or semi-viscous gel, ointment, cream, or other types of compositions. Preferably, the solution is administered topically either dropwise into the eye or to the tissue surrounding the eye. The solution or composition comprising the solution can also be formulated into a sterile solution for administration by intracameral injection into the anterior chamber of the eye or directly into the trabecular meshwork of the eye (e.g., for the treatment of dry or wet AMD). The doses used for the above described purposes can be determined by a physician or other qualified medical personnel and can depend, for example, on the type of ocular condition, the frequency of administration (i.e. for chronic or acute use), the severity of the condition, the age and overall health of the patient, the dosage form of the hypohalous acid, and other factors. For example, in one non-limiting embodiment, 1 to 2 drops of an HOCl solution is administered 1 to 10 times per day. In another embodiment, the solution is administered 1 to 4 times per day.

For prolonged, routine, or prophylactic use, one to two drops of the solution can be administered once or twice daily, similar to artificial tears. One non-limiting example of a chronic indication is using hypohalous acid drops for dry eyes or for rinsing or storing contact lenses. The hypohalous acid drops may be used to sooth/bath eyes from everyday wear and tear, such as, for example, from computer screen glare, dust and other environmental contaminants, exposure to air-conditioning, general dryness and other causes. The AFC concentration of the hypohalous acid solution may vary depending on whether the solution is used chronically or acutely. For example, for chronic use, the AFC concentration may be relatively low. For example, in certain embodiments, the AFC concentration is from about 5 to about 100 ppm, such as from about 5 to about 20 ppm. For acute use, such as an acute microbial infection, the AFC concentration should be sufficient to kill or reduce bacteria associated with the infection. Thus, for acute uses, the AFC concentration may be relatively high. For example, in certain embodiments, the AFC concentration is from about 200 to about 650 ppm. In certain other embodiments, the AFC concentration is from about 200 to about 400 ppm.

The present invention provides treatments as well as preventive care for conditions characterized by infection and/or inflammation of the ears (including the outer ear, middle ear, and inner ear), nose (including sinus care), mouth, and throat. Exemplary conditions include: rhinitis, rhinorrhea, nasal congestion, otitis media, external otitis, pharyngitis, and stomatitis, and may be present in a human or animal patient. The present invention further provides preventive care for such conditions, especially where such conditions are recurring, such as recurring ear infection, sinus infection, sore throat, or mouth ulcer.

In some embodiments, the composition is applied to treat or prevent rhinitis, rhinorrhea, or nasal congestion. Rhinitis, an inflammation of the nasal mucous membrane, may produce nasal decongestion and rhinorrhea. Rhinitis is typically of viral origin, but may involve secondary bacterial infection. Rhinorrhea and nasal congestion are typically of viral or allergic origin. In certain instances, congestion is observed as an after-effect of topical decongestants (rhinitis medicamentosa). While topical or oral decongestants (e.g., pseudoephedrine) can provide some symptomatic relief, prolonged use is not recommended.

In some embodiments, the composition is administered to treat otitis media or external otitis. Otitis media, inflammation of the middle ear structures, can lead to loss of equilibrium and deafness. Otitis media is generally of bacterial or viral origin. Viral infections may spawn secondary bacterial infections, including infections of *Streptococcus pneumonia, Moraxella catarrhalis*, and non-typable *Haemophilus influenzae*. External otitis is an acute or chronic inflammation of the external ear canal, and may involve bacterial (e.g., *Pseudomonas aeruginosa, Proteus vulgaris*, and *Staphylococcus aureus*) or fungal (e.g., *Aspergillus* and *Candida*) infection.

In still other embodiments, the composition is administered to treat or prevent pharyngitis (sore throat) or stomatitis. Pharyngitis is characterized by pain and swelling in the posterior pharynx. Pharyngitis is commonly caused by bacterial (e.g., Streptococcal) or viral infection. Stomatitis is a painful ulcer or inflammation of the oral mucosa. Stomatitis may be caused, for example, by infection (bacterial, viral, or fungal), chemical irritant, or allergic reaction, and may be common for patients having Xerostomia. Some common infectious agents include herpes simplex virus, varicella zoster, Epstein-Barr virus, influenza, cytomegalovirus, Gonorrhea, and *Candida*.

In these embodiments, the invention includes the treatment and prevention of infections caused by a variety of pathogens, such as, for example, a bacterial agent, a viral agent, a parasitic agent, and/or a fungal agent. Non-limiting examples of bacterial agents include *Streptococcus* spp. (e.g. *pneumoniae*), *Staphylococcus* spp. (e.g., *aureus* including MRSA), *Haemophilus* spp. (e.g., *influenzae*), *Moraxella* spp., *Pseudomonas* spp. (e.g., *aeruginosa*), *Chlamydia* spp. (e.g., *trachomatis, psittaci, pecorum*), *Neisseria* spp. (e.g. meningiditis), *Mycobacterium*, and *Actinomyces* species. Non-limiting examples of viral agents include adenovirus, respiratory syncytial virus (RSV), influenza (including parainfluenza and avian flu), coxackie virus, rhinovirus, coronavirus, varicella zoster, and herpes simplex virus. Non-limiting examples of fungal agents include *Candida* species, *Fusariu* species, and *Aspergillus* species.

In certain embodiments of the invention, the condition of the ear, nose, mouth, and/or throat involves a bacterial infection that is antibiotic resistant. For example, the bacterial infection may be resistant to antibiotics commonly employed to combat such infections either topically or systemically, such as sulfacetamide, erythromycin, gentamicin, ciprofloxacin, ofloxacin, cefoxitin, ceftriaxone, cefotaxime, spectinomycin, tetracycline, doxycycline, azithromycin, or bacitracin. In these and other embodiments, the bacterial invention may be resistant to beta-lactam antibiotics or fluoroquinolones. For example, the infection may involve methicillin-resistant *Staphylococcus aureus* (MRSA), for which the present invention is effective. Further, the invention may help control the presence and/or spread of MRSA in and from colonized individuals, that is, where no obvious infection is present. Thus, in some embodiments, the hypohalous acid is employed after antibiotic treatment to kill resistant pathogens, despite no remaining signs of infection.

In certain embodiments, the condition involves a viral infection with secondary bacterial infection (which may be antibiotic resistant), such that conventional antibiotic treatment is necessarily insufficient. For example, the condition may be a sinus infection or ear infection of viral origin, which has developed a bacterial superinfection. Unlike convention antibiotics, the invention has benefit in controlling and clearing both the viral and bacterial components of the infection.

In certain embodiments, the condition may involve a bacterial infection that produces a discharge, for example, external otitis or otorrhea. In these embodiments, the hypohalous acid effectively cleans discharge, biofilm, or debris from the ear in a manner that reduces the risk of spreading infection.

In certain embodiments, the condition involves an inflammatory disorder or hypersensitivity reaction (including types I, II, III, and/or IV). For example, the condition may involve an immediate-type hypersensitivity reaction such as allergic rhinitis or sinusitis. In other embodiments, the condition may result from a chronic inflammatory condition, which may also develop an acute bacterial infection. Such conditions may be recurring or may be difficult to completely clear.

Treating a condition of the skin, ear, nose, mouth, and/or throat in accordance with aspects of the present invention generally involves alleviating the cause or symptoms of the condition, and can include: reducing inflammation or hypersensitivity; reducing irritation; reducing discharge; clearing a microbial infection; preventing, or reducing the spread of a microbial infection. These can be measured or determined by comparing the patient's condition prior to and after treatment with hypohalous acid in accordance with the present invention. Alternatively, treatment can be determined relative to a patient having the same or similar condition who has not been treated with the hypohalous acid in accordance with the present invention. In certain embodiments, the administration of hypohalous acid treats both an infection and inflammation, such as acute or chronic inflammation.

In certain other embodiments, the hypohalous acid is administered prophylacticly, especially where infections are likely to occur or be transmitted among persons. Thus, in this embodiment, the invention involves administering the hypohalous acid before an infection develops. Such prophylactic care might include routine cleaning of the ear, mouth, throat, nose, or sinuses, with the hypohalous acid. Such embodiments can result in the prevention of an infection, can prevent the worsening of an existing infection, or can prevent irritation caused by bacterial biofilm.

In certain embodiments, the condition may be a bacterial infection that produces a discharge, such as an ear or sinus infection. In these embodiments, cleaning the middle ear, ear canal, or sinuses, for example, with the hypohalous acid of the invention provides the benefit of effectively cleaning wax, debris, biofilm, and/or discharge in a manner that reduces the risk of spreading the infection to another individual. Where the condition involves biofilm, the hypohalous acid deactivates the polymatrix material of the biofilm to facilitate removal (cleansing), and disinfection. Hypohalous acid contact with biofilm formation dissolves the protective polysaccharaide matrix of the biofilm aiding in the effective removal of pathogens and debris.

In certain embodiments, the condition may result from an acute or chronic inflammatory condition, which may develop an acute infection. In these embodiments, the hypohalous acid is administered to treat both the infection and the underlying inflammation. Thus, the hypohalous acid may be administered instead of steroidal drops or systemic steroidal medications, or antibiotics, thereby avoiding the potential adverse reactions of such treatments. In certain other embodiments, the hypohalous acid is used to clean the region during the duration of steroidal and/or antibiotic treatment. In one embodiment, hypohalous acid is administered to the nasal passages and/or sinuses of an allergic patient, during the duration of steroid treatment. For example, the hypohalous acid may be used in conjunction with steroid treatment, or alongside an antihistamine to more effectively inhibit release of inflammatory mediators from mast cells.

The hypohalous acid and compositions of the present invention may be administered in any appropriate dosage form such as a liquid, aerosol, or semi-solid including a solution, suspension, gas, viscous or semi-viscous gel, ointment, cream, or other types of compositions. Such compositions include nasal sprays, throat sprays, and mouth wash. The doses used for the above described purposes can be determined by a physician or other qualified medical personnel and can depend, for example, on the type of condition, the frequency of administration (i.e. for chronic or acute use), the severity of the condition, the age and overall health of the patient, the dosage form of the hypohalous acid, and other factors. For example, in one non-limiting embodiment, 1 to 2 drops of the hypohalous acid solution is administered 1 to 10 times per day. In another embodiment, the solution is administered 1 to 4 times per day.

For prolonged, routine, or prophylactic use, one to two drops of the solution can be administered once or twice daily. The AFC concentration of the hypohalous acid solution may vary depending on whether the solution is used chronically or acutely. For example, for chronic use, the AFC concentration may be on the lower end of a range from 5 to 1000. For example, in certain embodiments, the AFC concentration is from about 5 to about 100 ppm, such as from about 5 to about 20 ppm. For acute use, such as an acute microbial infection, the AFC concentration should be sufficient to kill or reduce bacteria associated with the infection. The AFC concentration is preferably on the higher end of a range from 5 to 1000 ppm, or a range of from 5 to 5000 ppm. For example, in certain embodiments, the AFC concentration is from about 200 to about 650 ppm. In certain other embodiments, the AFC concentration is from about 200 to about 400 ppm.

For patients afflicted with a sinus infection and/or allergic condition, the present invention provides for administration of the hypohalous acid as described herein to the nose and/or sinus cavity. In these embodiments, the invention provides a broadly effective and safe treatment for sinus conditions characterized by infection and/or inflammation (including immediate-type hypersensitivity), so as to avoid development of bacterial resistance to antibiotics, and so as to avoid toxicity, adverse effects, irritation, and/or hypersensitivity that may occur with other agents including antihistamines. In these embodiments, the hypohalous acid as described herein may be administered to the nose or sinuses of an affected patient as an alternative or adjunct therapy to antibiotics and/or antihistamines, or other convention treatment, depending on the suspected etiology of the condition. In accordance with these embodiments, the hypohalous acid may be administered as a nasal spray using conventional formulation as described in U.S. Pat. No. 6,565,832, for example, which is hereby incorporated by reference in its entirety.

In another embodiment, the hypohalous acid treatment is followed by treatment with an antioxidant, such as a vitamin.

The hypohalous acid solution for use in the methods and compositions of the present invention may be prepared by chemical acidification or dilution (e.g., of hypochlorites) or by electrolysis of a salt solution. Exemplary methods and apparatuses for preparing electrolyzed solutions are disclosed in US published patent application no. 2004/0060815, which is hereby incorporated by reference in its entirety.

In one embodiment, a salt solution (electrolyte) may be pre-packaged and provided for preparing the hypohalous acid solution on demand by electrolysis. In other embodiments, the electrolyte may be provided in dry form, and mixed with de-ionized and/or softened water to prepare the hypohalous acid on demand.

FIG. 1 provides a schematic outline of the main processing stages of a non-limiting, exemplary method for producing an electrolyzed saline solution. Such a method involves an input and pre-processing stage; a production stage; and a storage and dispensing stage. In the input and pre-processing stage, water can be passed through a water softener zone where excess magnesium and calcium ions are removed. The resultant softened water can be passed as process water to a brine generation zone where a salt (e.g., a halide salt such as NaCl and/or KCl) can be added to produce a dilute salt solution. Preferably, the salt is vacuum dried crystalline salt which is commercially produced to a consistent standard. The dilute salt solution can be a substantially constant concentration since a known quantity of salt is added to a known quantity of softened water to achieve a desired concentration of the dilute salt solution. Another method may involve mixing a known amount of a salt, such as, for example, NaCl or KCl, with de-ionized or de-mineralized water. This water can be used as delivered by a deionizer or demineralizer or can be dosed with a known amount of a buffering agent, such as, for example, sodium bicarbonate. This electrolyte can then be introduced to the production stage.

Figure 2:
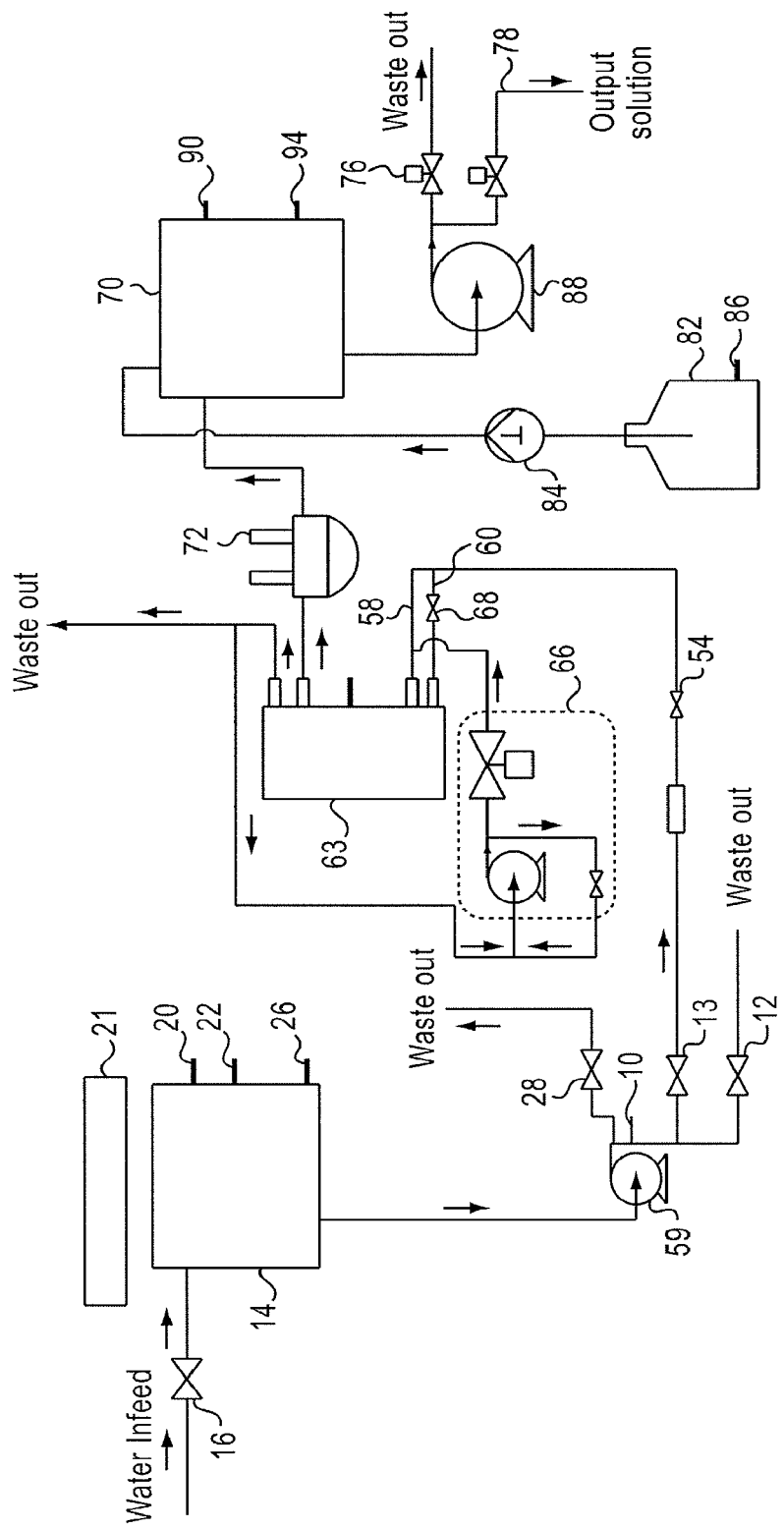
FIG. 2 is a flow diagram depicting the production of an electrolyzed saline solution for use in accordance with certain embodiments of the present invention.
Figure 3:
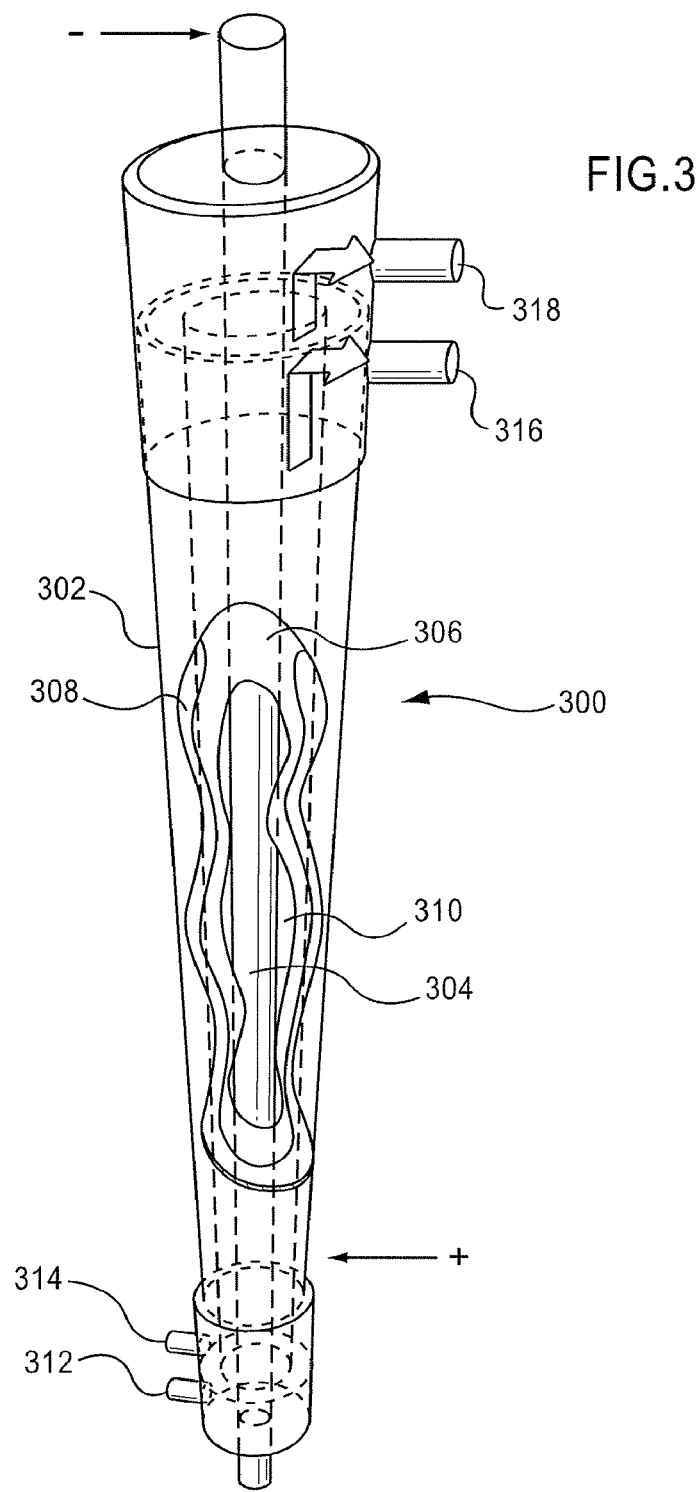
FIG. 3 is a schematic illustration of an electrochemical cell that may be used to produce an electrolyzed saline solution.

In the production stage, the dilute saline solution or prepared electrolyte can be passed to one or more electrolytic cell systems, such as the electrolytic cell pack 63 depicted in FIG. 2 (a preferred embodiment of which is described in more detail in FIG. 3). Of course, other electrolytic systems can be used as well such as parallel discs and parallel plate systems. The electrochemical cell includes a cathode and an anode chamber, across which a substantially constant electric current is applied. The applied electric current can be maintained constant via an energy control and monitoring zone. Catholyte and anolyte are produced from the cathode and anode chambers respectively as a result of electrochemical treatment of the saline solution in the cells. Catholyte and anolyte can be prevented from mixing using a separator. For example, a semi-permeable membrane can be used in the case of parallel plate technology (for example, NAFION membrane) or a porous ceramic membrane. In some embodiments, the catholyte is not required for the final solution and is directed to drain. In other embodiments, all or part of the catholyte is re-introduced into the anode chamber (referred to in the art as catholyte recirculation). Catholyte that is not recirculated can be directed to waste, and anolyte, otherwise referred to as output solution, is passed to a buffer storage and quality subsystem in the storage and dispensing stage. The output solution can be tested in the buffer storage and quality subsystem, and, if it fails to meet the quality standards, can also be directed to waste. If the output solution falls within specification, the output solution can be permitted to pass to an output solution storage zone from where it can be subsequently dispensed for use or packaged.

FIG. 2 is a flow diagram or "hydraulic map" showing in more detail an exemplary method of producing an electrolyzed saline solution in accordance with the present invention. Potable water can be passed through an external water softener containing a cation exchange resin (not shown) thereby exchanging hardness ions of calcium and magnesium onto the resin and releasing sodium ions into the water. The softened water can be fed through a valve 16 into a softened water tank 14 which may include a plurality of level detectors for monitoring and controlling the softened water level. For example, tank 14 may include a level detector 20, which is a safety device which is activated only when the softened water in tank 14 reaches a predetermined extra high level to stop the charging of tank 14 with further softened water. Tank 14 may also include a level detector 22 which ensures that tank 14 has a correct volume of softened water to prepare the appropriate concentration of saline solution. Tank 14 may also include a level detector 26 and softened water will begin to re-charge tank 14 when the softened water drops below a predetermined low level determined by level detector 26 and at the end of production of one batch of electrolyzed saline solution. Tank 14 may also include a valve 28 which allows liquid to be drained.

To produce a saline solution from the softened water in tank 14, a salt, such as, for example, vacuum dried crystalline salt can be added to tank 14 via dispensing wheel 21. Dispensing wheel 21 contains many tablets of known salt mass, a pre-determined number of which are dispensed through a hole in the top of tank 14 at the start of each electrolyzed saline solution production cycle. Preferably, the saline solution has a salt concentration range of 2.0 to 90.0 g/L.

Pump 59 can pump the saline solution towards an electrolytic cell pack 63. The flow rate of the saline solution can be monitored by a sensor 10. The sensor can ascertain whether the incoming saline solution is at a temperature within the range under which the process can reasonably operate, such as between 5 and 35° C. Other parameters such as the incoming solution's pressure, softness, alkalinity, pH, conductivity, and microbial count can be monitored, modulated and/or controlled to establish that the solution falls within acceptable levels for the process or for desired characteristics of the resulting solution. For example, as the salt concentration of the solution is increased, the conductivity can be increased and other parameters, such as the current, would change. The various parameters can be modified to correspond to the desired salt concentration of the solution. A person of skill in the art can appreciate whether the incoming water is not suitable for processing according to embodiments of the present invention. If sensor 10 detects that the properties of the incoming saline solution do not fall within acceptable limits, the solution can be diverted through a waste discharge manifold (not shown) to a drain via valve 12. On the other hand, if the incoming saline solution is acceptable, it can be allowed to flow into the cells through valve 13.

The saline solution can then split into two streams 58 and 60 before being fed through electrochemical cell pack 63. In certain embodiments, electrochemical cell pack 63 can include eight electrolytic cells, with two sets of four cells connected hydraulically in parallel. For simplicity, only one cell is illustrated. In general, the number of cells in the cell pack can be determined by the output volume required from the particular system. Each cell has an anode chamber and a cathode chamber and the flow of saline solution can be split such that the greater portion is fed to the anode chamber and the lesser portion is fed to the cathode chamber. In certain embodiments, approximately 90% of the saline solution can be passed through the anode chamber and the remainder can be passed through the cathode chamber. The flow rate of saline solution through the cathode chamber can be much lower than for the anode chamber and the pressure in the cathode chamber can also be lower. The flow rate of saline solution into the cathode chamber, which also has an influence on the pH of the output solution, can be controlled by a flow regulator 68. Flow regulator 68 can be manually adjusted if there is a variation in input water quality.

In certain embodiments, the flow rate supplied to the anode is from 50% to 95%, inclusive of all intermediate values, of the solution applied to the electrolytic cell pack 63. In certain embodiments, the flow rate to the anode is from 85% to 95% of the solution supplied to the electrolytic cell pack.

As the saline solution flows through the electrolytic cells, a fixed current of from 0.1 to 25 amps, preferably 15 to 25 amps, and more preferably 18-19 amps, can be applied to each cell causing electrolysis of the saline solution thereby generating available free chlorine in the resulting anolyte, elsewhere generally referred to as the output solution. In order to produce output solution at a certain pH, for example between 5 and 7 (acidic to neutral), the pH of the output solution may be at least partially controlled by dosing a portion of the catholyte to the inlet stream for the anode chambers. The catholyte may be dosed to the inlet stream 58 by an adjustable pump and valve system 66 and the dosing rate is increased or decreased to achieve the target pH. The remaining catholyte which is not dosed into the input stream 58 for the anode chambers can be directed to waste, if necessary diluting it prior to disposal. As just described, in certain embodiments, the catholyte can be dosed into the anode stream 58 before this stream enters the anode. However, the catholyte can also be dosed into the anode stream after it has been electrolyzed. In those application where the electrolyte is prepared by mixing the various salts with de-ionized or de-mineralized water, mixing of the catholyte may not be performed, in which case all the catholyte is diverted to drain. If a proportion of the catholyte is used for pH control, then the catholyte can be dosed to the anode stream either before or after it enters the anode chamber.

The output solution can then be directed to tank 70. The pH of such output solution can be measured by a meter 72. If the pH does not fall within the desired parameters, a valve 76 can be opened and the contents of tank 70 can be drained to waste. Meter 72 can be linked to a pump and valve system 66 to adjust the level of catholyte dosed to the anode chambers thereby enabling the pH of the output solution to be adjusted to bring the output solution within the desired pH range. If the pH of the output solution is determined to fall within the desired parameters, valve 76 can be kept closed and the output solution can be allowed to fill tank 70. Other properties of the output solution, such as redox potential or AFC, could also form the basis of the measurement and control system consisting of meter 72 and adjustable pump and valve system 66.

Storage tank 70 may include various level detectors for monitoring liquid levels in the tank. For example, a level detector 90 may be activated by an extra high level of output solution within the tank, raising an alarm and stopping production. Low level detector 94 may be activated when the level of the output solution falls to a low level, raising an alarm and preventing further dispensing to the appropriate receptacle. As the output solution is dispensed and after a period of time below the level of detector 94, production of output solution may be re-commenced. From the storage tank, the output solution can be distributed in individual nebulizers, inhalers, or ampules. Where the electrolyzed solution is to be administered by humidifier or misting, the electrolytic cell system may be functionally coupled to a humidifier or fogger. Of course, the above-described processing steps of producing an electrolyzed saline solution are only exemplary and other electrochemical processes could be used to produce an electrolyzed saline solution of embodiments of the present invention.

FIG. 3 shows an embodiment of an electrolytic cell 300 used in certain methods of producing an electrolyzed saline solution according to an embodiment of the present invention. In this embodiment, cell 300 comprises co-axial cylindrical and rod electrodes 302, 304 respectively, separated by a semi-permeable ceramic membrane 306 co-axially mounted between the electrodes thus splitting the space between the electrodes to form two chambers 308 and 310. Cylindrical electrode 302, which is this embodiment forms the anode, is typically made from commercially pure titanium coated with a ruthenium oxide and iridium oxide-based electrocatalytic (active) coating suitable for the evolution of chlorine from a chloride solution. Rod electrode 304, which in this embodiment forms the cathode, is typically made from titanium and can be machined from an 8 mm stock bar to a uniform cross-section over its effective length, which is typically about 210 mm+0.5 mm. Of course, it will be understood by one of skill in the art that other suitable materials and configurations can be used to fabricate electrodes 302 and 304 to allow these electrodes to perform their necessary function. Also, either electrode can serve as the anode and similarly either electrode can serve as the cathode. If the rod is used as an anode, it is coated with a coating, such as ruthenium oxide and iridium oxide based electrocatalytic (active) coating, for example, suitable for the evolution of chlorine from a chloride solution. Semi-permeable ceramic membrane 306 forming a separator and creating the anode and cathode chambers 308 and 310 can be composed of aluminum oxide (80%), zirconium oxide (18.5%) and yttrium oxide (1.5%), and preferably has a porosity of about 50-70%, a pore size of 0.3 to 0.5 microns and a wall thickness of 0.5 mm+0.3 mm/−0.1 mm. The ceramic of certain embodiments of membrane 306 is described in the specification of patent application GB 2354478 (Sterilox Medical (Europe) Limited), the subject matter of which is incorporated herein by reference. Ceramic membrane 306 can be made of any other suitable semi-permeable or ion-selective material of ceramics other than the aluminum oxide, zirconium oxide and yttrium oxide ceramic described above.

Generally, the surface area of the anode can be largely defined by the quantities of output solution desired to be produced and available free chlorine content desired in that solution. However, in order to provide a system that is of a size appropriate for commercial installation and to produce the quantities of antimicrobial solution of the invention often required, an anode surface area of 0.065 to 0.095 m$^2$, inclusive of all intermediate values, can be utilized. Such a surface area can be made up by a number of electrolytic cells working in parallel. An anode area of 0.070 to 0.090 m$^2$ is more preferable, and an anode surface area of 0.075 to 0.085 m$^2$ is even more preferable. In certain embodiments, eight cells are arranged in parallel and the current density on the surface of each anode is within the range 1.5 to 2.5 kAm$^{-2}$, more preferably 1.7 to 2.2 kAm$^{-2}$, and still more preferably 1.85 to 1.95 kAm$^2$.

In this embodiment, cell 300 is provided with entry passages 312 and 314 to permit the saline solution to enter cell 300 and flow upwards through the anode and cathode chambers 308 and 310 to be discharged as anolyte and catholyte through exit passages 316 and 318 respectively. The anolyte containing available free chlorine constitutes the output solution.

As previously described in reference to FIG. 2, in certain embodiments, in order to provide a preferred amount of output solution within a reasonable period of time, a group of cells can be connected together to form a cell pack 63. For example, a cell pack comprising eight cells connected together in parallel hydraulically and in series electrically may generate about 200 liters/hour of output solution.

When using higher volume generators, the flow rate through the anode chamber may vary between 100 to 220 l/h. For example, the flow rate may be 150 to 210 l/h, or may be 185 to 205 l/h is even more preferred. The flow rate can also be any value within the expressed ranges. Using lower volume generators, the flow rate through the anode chamber may be in the range of 10-50 l/h, such as, for example, 30 l/h. The person skilled in the art will appreciate that the flow rate can be altered beyond such a range but still produce the solution of embodiments of the invention by varying the number of cells/surface area of anode. For example, the flow rate per anode surface area of $1.25 \times 10^3$ to $2.75 \times 10^3$ lh$^{-1}$ m$^{-2}$ can be used produce an embodiment of an electrolyzed saline solution of the invention. The flow rate can also take any value with the aforementioned range. Preferably, the flow rate is $1.87 \times 10^3$ to $2.63 \times 10^3$ lh$^1$ m$^{-2}$ and more preferably the flow rate is $2.31 \times 10^3$ to $2.56 \times 10^3$ lh$^{-1}$ m$^{-2}$. The skilled person can obtain the required current to produce a suitable solution by setting the flow rate to that just described and varying the current until the solution produced has the suitable specifications.

In certain embodiments, the current range is 15 to 25 A, inclusive of all intermediate values. In certain embodiments, a current range of 17 to 22 A is used and in certain embodiments a current range of 18.5 to 19.5 A is used. When using higher volume generators, with the flow rate through the anode chamber between 100 to 220 l/h, the current range of 70-100 A can be used as well, in that case hypochlorous acid solution with low ionic strength, or low saline concentration is produced.

The residual salt concentration of an embodiment of an electrolyzed saline solution can be from 2.0 g/l to 90 g/l, and in some cases from 1 to 2 g/l. This residual salt concentration can result from the entire desired amount of salt being added during the input and pre-processing stage or less than the entire desired amount of salt being added during the input and pre-processing stage and the remainder of the desired amount of salt being added after the production stage. Solution with lower ionic strength could be preferable for hypochlorous acid compositions applied in form of cream, emulsion, gel, or foam.

EXAMPLES

Ocular Irritation

An eye irritation study was conducted on six healthy New Zealand white rabbits, free from evidence of ocular irritation and corneal abnormalities. The test article (0.1 ml hypochlorous acid, 689.5 ppm AFC) was placed into the conjunctival sac of one eye of each rabbit. The contralateral eye served as a control. The eyes were examined and scored by the Draize technique for any evidence of irritation or abnormalities of the cornea, on days 1, 2, and 3 post dose. The primary eye irritation score of each rabbit, each day was calculated. All eyes appeared normal at each observation period and there were no abnormal physical signs noted. In conclusion, under the test conditions of this study, hypochlorous acid (689.5 ppm AFC) showed no ocular irritation.

Dermal Irritation

A skin irritation study was conducted on six healthy New Zealand white rabbits. The test article (0.5 ml hypochlorous acid, 689.5 ppm AFC) was applied to one intact and one abraded site on the clipped back of each rabbit. Skin reactions were evaluated by the Draize technique at 24 and 72 hours after dosing and the primary irritation index was calculated. There was no erythema or edema noted at any time period and there were no abnormal physical signs noted during the observation period. In conclusion, under the test conditions of this study, hypochlorous acid (689.5 ppm AFC) showed no dermal irritation.

Skin Sensitization

A skin sensitization study was conducted on ten test and five control albino guinea pigs. The method used was the Magnusson and Kligman guinea-pig maximization model. The animals were dosed (hypochlorous acid, 241-252 ppm AFC) by intradermal injection and by topical application. Following initial exposure to the test substance, the animals were subjected to approximately two weeks after topical induction to a "challenge" exposure of the test substance (50% v/v) in order to establish whether a hypersensitivity state had been induced. In this study, there was no evidence of delayed contact hypersensitivity. In conclusion, under the test conditions, hypochlorous acid (241-252 ppm AFC) demonstrated no skin sensitization.

Delayed Dermal Sensitization in Guinea Pig Maximization Test

Hypochlorous acid solution (700 ppm AFC) and Hypochlorous Acid Sprayable Hydrogel (500 ppm AFC) were evaluated for delayed dermal contact sensitization. Hypochlorous acid solution (690 ppm AFC) was intradermally injected and occlusively patched to test guinea pigs in an attempt to induce sensitization. The control article, 0.45% Sodium Chloride USP solution, was similarly injected and occlusively patched to five control guinea pigs. Following recovery period, the test and control animals received challenge patches of the test solution and the control article. All sites were scored at 24 and 48 hours after patch removal. Under the conditions of this study, hypochlorous acid solution (690 ppm AFC) showed no evidence of causing a delayed dermal contact sensitization in the guinea pig.

Hypochlorous Acid Sprayable Hydrogel (500 ppm AFC) was evaluated for the potential to cause delayed dermal contact sensitization in the Harley albino guinea pigs (15 females). The test article was intradermally injected and occlusively patched to ten guinea pigs. The control article was similarly injected and occlusively patched to five control guinea pigs. Following a recovery period, the test and control animals received challenge patches of the test solution and the vehicle control article. All sites were scored for dermal reaction at 24 and 48 hours after patch removal.

The test articles, Hypochlorous Acid Sprayable Hydrogel (500 ppm AFC), showed no evidence of causing delayed dermal contact sensitization in the guinea pig. Thus it was not considered a sensitizer in the guinea pig maximization test.

Acute Oral Toxicity

The test articles, hypochlorous acid solution (500 ppm AFC) and hypochlorous acid composition in form of sprayable gel (500 ppm AFC), were evaluated for oral toxicity in rats. Only healthy, previously unused animals were selected. A single dose of 5 g/kg body weight was orally given to 10 rats in each study. The animals were observed immediately after dosing, at 4 hours, and daily up to 14 days for signs of illness or mortality. Body weights were recorded at dosing and at 14 days for survivors. Animals found dead during study or those euthanized by carbon dioxide inhalation at termination of the study were subjected to a macroscopic examination of the viscera. Based on the FHSA Regulations, a substance is considered "toxic" if it produces death within 14 days in 50% or more of a group of rats dosed with a single 50 mg/kg to 5 g/kg dose.

There was no mortality or evidence of toxicity observed in the rats. The test articles, hypochlorous acid solution (500 ppm AFC) and hypochlorous acid composition in form of sprayable gel (500 ppm AFC), were not considered as toxic at a dose of 5 g/kg by the oral route in the rats.

Vaginal Irritation Study

Vaginal Irritation of hypochlorous acid composition in form of sprayable gel was conducted in accordance with the requirements of ISO 10993-10, Biological Evaluation of Medical Devices: Tests for irritation and skin sensitization.

Hypochlorous acid composition in form of sprayable gel (500 ppm Available Free Chlorine) was evaluated for the potential to cause irritation to vaginal tissue after being administered intravaginally to rabbits for 5 consecutive days. Healthy animals were selected. To reduce the number of animal used for testing, animals used previously in an untreated test model were assigned to the control treatment group. Three animals each received a single 1 mL instillation of the test article into vagina. Three control animals received a similar dose of 0.9% sodium chloride USP solution. The appropriate dose of test or control article was introduced into the vagina vault through a blunt tipped cannula moistened with the preparation or a suitable lubricant. Animals were returned to their cages after treatment. Statistical evaluation of the data was not concluded. Macroscopic observations of the vaginal tissue were compared between test and control animals. Cellular changes were graded according to severity (0-4). The microscopic evaluation scores for all test animals were added together and divided by the number of test animals to obtain the test group average. The control group average was similarly calculated. The control group average was subtracted from the test group average to obtain the Irritation index.

Hypochlrous acid composition in form of sprayable gel (500 ppm AFC), was considered a minimal irritant to vaginal tissue of rabbit.

Bacterial Mutagenicity

In vitro assessment of the mutagenic potential of hypochlorous acid (241-252 ppm AFC) was examined using histidine dependent auxotrophice mutants of *Salmonella typhimuium* (strains TA1535, TA1537, TA98 and TA100 and a tryptophan dependent mutant of *Escherichia coli* (strain CM891) were exposed to the test substance. Mutation assays were performed in the absence and presence of liver S9 fraction preparations from Aroclor 1254-induced rats. No evidence of mutagenic activity was observed with hypochlorous acid at the test concentration of 241-252 ppm.

In Vitro Microbiology Profile

Hypochlorous acid has rapid virucidal, bactericidal, sporicidal and fungicidal activity. It rapidly kills gram positive and gram negative bacteria, including antibiotic resistant species of MRSA and VRE. MRSA skin infections are becoming more prevalent and there is a perceived need for alternative medications for patients who are infected by MRSA. In vitro antimicrobial studies have shown hypochlorous acid to produce greater than log 5 kill within a 15 seconds contact time against a range of wound pathogens including *S. aureus, P. aeruginosa, E. coli, Enterococcus* spp., and *Candida* spp., even at concentrations of ≤150 ppm of hypochlorous acid (Table 1-4), including activity against bacterial endospores.

Results demonstrate that hypochlorous acid solution, when generated by electrolysis, is effective in laboratory suspension and carrier tests within a 15 seconds contact time against pathogens, including *Staphylococcus aureus, Escherichia coli, Pseudomonas aeruginosa, Enterococcus faecalis, Aspergillus* and *Candida albicans* (Table 2).

TABLE 1

Exemplary pathogens killed by hypochlorous acid 150 ppm, pH 6.3-6/75

| Bacteria | Bacterial Endospores | Viruses | Fungi |
|---|---|---|---|
| *Pseudomonas aeruginosa* | *Bacillus cereus* | Adenovirus type V | *Aspergillus niger* |
| *Staphylococcus aureus* | *Bacillus subtilis* var | HIV-1 | *Candida albicans* |
| *Enterococcus faecium* (VRE) | *Clostridium sporogenes* | Poliovirus type 1 | *Trichophyton mentagrophytes* |
| *Salmonella choleraesuis* | | Human Flu virus | |
| | | Orthopoxvirus | |
| | | Human Norovirus | |
| | | Murine Norovirus | |
| | | MS2 coliphage virus | |

Bactericidal, Mycobactericidal, Fungicidal, Sporicidal, and Virucidal Suspension Tests Bactericidal activity suspension tests were performed using hypochlorous acid (at 140-180 ppm, Table 2) and hypochlorous acid compositions (at 40-45 ppm, Table 4) against *Staphylococcus aureus* ATCC 6538 and *Pseudomonas aeruginosa* ATCC 15442 and *Enterococcus faecium* ATCC 10541. Stock culture of *Staphylococcus aureus* ATCC 6538, *Pseudomonas aeruginosa* ATCC 15442 and *Enterococcus faecium* ATCC 10541 were grown and maintained on Tryptic Soy Agar at 37° C. Bacterial suspensions (1 ml) were added to 1 ml of 0.3% BSA and 8 ml of hypochlorous acid at a range of concentrations at 20° C. After an exposure time of 5 minutes, 1 ml samples were neutralized using universal quench. All samples were serially diluted, plated out on Tryptic Soy Agar, incubated at 37° C. for 3 days and colonies forming units counted.

Fungicidal activity tests were performed using hypochlorous acid (140-150 ppm) against *Candida albicans* ATCC 10231 and *Aspergillus niger* ATCC 16404. Stock culture of *Candida albicans* ATCC 10231 and *Aspergillus niger* ATCC 16404 were grown and maintained on Malt Extract Agar at 30° C. Fungal suspensions (1 ml) were added to 1 ml of sterile distilled water and 8 ml of hypochlorous acid solution at a range of concentrations at 20° C. After an exposure time of 5 minutes, 1 ml samples were neutralized using standard quench solution. All samples were serially diluted, plated out on Tryptic Soy Agar, incubated at 37° C. for 3 days and colonies forming units counted.

Sporicidal activity tests were performed using hypochlorous acid solution against *Bacillus cereus* CIP 7803, *Bacillus subtilis* CIP 7718, *Clostridium sporogenes* CIP 7939. Stock spore suspensions of *Bacillus cereus* CIP 7803, *Bacillus subtilis* CIP 7718, *Clostridium sporogenes* CIP 7939 were obtained from the Pasteur Institute's National Collection for the Culture of micro-organisms. Spore suspensions (1 ml) were added to 4 ml of sterile distilled water and 5 ml of hypochlorous acid solution at a range of concentrations at 20° C. After an exposure time of 60 minutes, 1 ml samples were neutralized using standard quench solution. All samples were serially diluted, plated out on selective agar, incubated aerobically or anaerobically at either 30° C. or 37° C. for 72 hours and colonies forming units counted.

TABLE 2

Microbial Time Kill Assay Results for HOCl solution, 150 ppm AFC (15 second contact time)

| Test Organism | Numbers Control | | HOCl Solution | | Log Reduction | % Reduction (% Kill) |
|---|---|---|---|---|---|---|
| | Survivors | $Log_{10}$ | Survivors | $Log_{10}$ | | |
| *Staphylococcus aureus* (MRSA) ATCC #33591 | $1.6 \times 10^6$ | 6.20 | <10 | ≤1 | ≥5.20 | >99.999% |
| *Enterococcus faecium* (VRE) ATCC #51559 | $1.6 \times 10^6$ | 6.20 | <10 | ≤1 | ≥5.20 | >99.999% |
| *Staphylococcus aureus* ATCC #6538 | $9.2 \times 10^5$ | 5.96 | <10 | ≤1 | ≥4.96 | >99.995% |
| *Escherichia coli* ATCC #8739 | $1.9 \times 10^6$ | 6.28 | <10 | ≤1 | ≥5.28 | >99.999% |
| *Acinetobacter baumannii* ATCC #19606 | $1.4 \times 10^6$ | 6.15 | <10 | ≤1 | ≥5.15 | >99.999% |
| *Bacteroides fragilis* ATCC #25285 | $4.6 \times 10^6$ | 6.66 | <10 | ≤1 | ≥5.66 | >99.999% |
| *Candida albicans* ATCC #10231 | $4.3 \times 10^6$ | 6.63 | <10 | ≤1 | ≥5.63 | >99.999% |
| *Enterobacter aerogenes* ATCC #51342 | $2.7 \times 10^6$ | 6.43 | <10 | ≤1 | ≥5.43 | >99.999% |
| *Enterococcus faecium* ATCC #35667 | $1.2 \times 10^6$ | 6.08 | <10 | ≤1 | ≥5.08 | >99.999% |
| *Haemophilus influenza* ATCC #8149eb;normal | $3.9 \times 10^6$ | 6.59 | <10 | ≤1 | ≥5.59 | >99.999% |

TABLE 2-continued

Microbial Time Kill Assay Results for HOCl solution, 150 ppm AFC
(15 second contact time)

| Test Organism | Numbers Control Survivors | $Log_{10}$ | HOCl Solution Survivors | $Log_{10}$ | Log Reduction | % Reduction (% Kill) |
|---|---|---|---|---|---|---|
| Klebsiella oxytoca ATCC #12833 | $1.5 \times 10^6$ | 6.18 | <10 | ≤1 | ≥5.18 | >99.999% |
| Klebsiella pneumonia ATCC #4352 | $5.0 \times 10^6$ | 6.70 | <10 | ≤1 | ≥5.70 | >99.999% |
| Micrococcus luteus ATCC #10240 | $1.1 \times 10^6$ | 6.04 | <10 | ≤1 | ≥5.04 | >99.999% |
| Proteus mirabilis ATCC #43071 | $4.0 \times 10^6$ | 6.40 | <10 | ≤1 | ≥5.40 | >99.999% |
| Pseudomonas aeruginosa ATCC #9027 | $1.3 \times 10^6$ | 6.11 | <10 | ≤1 | ≥5.11 | >99.999% |
| Serratia marcescens ATCC #14756 | $1.2 \times 10^6$ | 6.08 | <10 | ≤1 | ≥5.08 | >99.999% |
| Staphylococcus epidermidis ATCC #14990 | $4.9 \times 10^6$ | 6.69 | <10 | ≤1 | ≥5.69 | >99.999% |
| Staphylococcus haemolyticus ATCC #29968 | $3.7 \times 10^6$ | 6.57 | <10 | ≤1 | ≥5.57 | >99.999% |
| Staphylococcus hominis ATCC #25615 | $4.8 \times 10^6$ | 6.68 | <10 | ≤1 | ≥5.68 | >99.999% |
| Staphylococcus saprophyticus ATCC #15305 | $4.8 \times 10^6$ | 6.68 | <10 | ≤1 | ≥5.68 | >99.999% |
| Streptococcus pyogenes ATCC #19615 | $3.4 \times 10^6$ | 6.53 | <10 | ≤1 | ≥5.53 | >99.999% |

EndosporeTime Kill Assay

Results showed that hypochlorous acid solution at a concentration of less than 150 ppm AFC after 15 seconds contact time produced >99.9% reduction against *Clostridium difficile* endospores.

TABLE 3

Endospore Time Kill Assay Results for HOCl solution, ≤150 ppm AFC

| Test Organism | Numbers Control Survivors | $Log_{10}$ | Vashe Survivors | $Log_{10}$ | Log Reduction | % Reduction (% Kill) | Contact Time |
|---|---|---|---|---|---|---|---|
| Clostridium difficile (spores) | $4.7 \times 10^5$ | 5.67 | 330 | 2.52 | 3.15 | 99.93% | 15 seconds |
| Clostridium difficile (spores) | $4.9 \times 10^6$ | 6.69 | <10 | ≤1 | ≥5.69 | >99.999% | 5 minutes |

TABLE 4

Microbial Time Kill Assay Results for HOCl composition in form of sprayable hydrogel, ≤45 ppm AFC (30 sec. contact time)

| Test Organism | Numbers Control Survivors | $Log_{10}$ | Vashe Solution Survivors | $Log_{10}$ | Log Reduction | % Reduction (% Kill) |
|---|---|---|---|---|---|---|
| Staphylococcus aureus (MRSA) ATCC #33591 | $4.8 \times 10^6$ | 6.68 | <10 | ≤1 | ≥5.68 | >99.999% |
| Enterococcus faecium (VRE) ATCC #51559 | $1.1 \times 10^6$ | 6.04 | <10 | ≤1 | ≥5.04 | >99.999% |
| Staphylococcus aureus ATCC #6538 | $1.4 \times 10^6$ | 6.15 | <10 | ≤1 | ≥5.15 | >99.999% |

TABLE 4-continued

Microbial Time Kill Assay Results for HOCl composition in form of sprayable hydrogel, ≤45 ppm AFC (30 sec. contact time)

| Test Organism | Numbers Control Survivors | $Log_{10}$ | Vashe Solution Survivors | $Log_{10}$ | Log Reduction | % Reduction (% Kill) |
|---|---|---|---|---|---|---|
| *Escherichia coli* ATCC #8739 | $1.5 \times 10^6$ | 6.18 | <10 | ≤1 | ≥5.18 | >99.999% |
| *Acinetobacter baumannii* ATCC #19606 | $1.0 \times 10^6$ | 6.00 | <10 | ≤1 | ≥5.00 | >99.999% |
| *Bacteroides fragilis* ATCC #25285 | $2.2 \times 10^6$ | 6.34 | <10 | ≤1 | ≥5.34 | >99.999% |
| *Candida albicans* ATCC #10231 | $1.0 \times 10^6$ | 6.00 | <10 | ≤1 | ≥5.00 | >99.999% |
| *Enterobacter aerogenes* ATCC #51342 | $1.3 \times 10^6$ | 6.11 | <10 | ≤1 | ≥5.11 | >99.999% |
| *Enterococcus faecium* ATCC #35667 | $1.2 \times 10^6$ | 6.08 | <10 | ≤1 | ≥5.08 | >99.999% |
| *Haemophilus influenza* ATCC #8149 | $5.4 \times 10^6$ | 6.73 | <10 | ≤1 | ≥5.73 | >99.999% |
| *Klebsiella oxytoca* ATCC #12833 | $1.1 \times 10^6$ | 6.04 | <10 | ≤1 | ≥5.04 | >99.999% |
| *Klebsiella pneumonia* ATCC #4352 | $4.3 \times 10^6$ | 6.63 | <10 | ≤1 | ≥5.63 | >99.999% |
| *Micrococcus luteus* ATCC #10240 | $1.1 \times 10^6$ | 6.04 | <10 | ≤1 | ≥5.04 | >99.999% |
| *Proteus mirabilis* ATCC #43071 | $1.1 \times 10^6$ | 6.04 | <10 | ≤1 | ≥5.04 | >99.999% |
| *Pseudomonas aeruginosa* ATCC #9027 | $1.4 \times 10^6$ | 6.15 | <10 | ≤1 | ≥5.15 | >99.999% |
| *Serratia marcescens* ATCC #14756 | $1.4 \times 10^6$ | 6.15 | <10 | ≤1 | ≥5.15 | >99.999% |
| *Staphylococcus epidermidis* ATCC #14990 | $4.6 \times 10^6$ | 6.66 | <10 | ≤1 | ≥5.66 | >99.999% |
| *Staphylococcus haemolyticus* ATCC #29968 | $1.1 \times 10^6$ | 6.52 | <10 | ≤1 | ≥5.52 | >99.999% |
| *Staphylococcus hominis* ATCC #25615 | $3.3 \times 10^6$ | 6.68 | <10 | ≤1 | ≥5.68 | >99.999% |
| *Staphylococcus saprophyticus* ATCC #15305 | $2.0 \times 10^6$ | 6.30 | <10 | ≤1 | ≥5.30 | >99.999% |
| *Streptococcus pyogenes* ATCC #19615 | $3.4 \times 10^6$ | 6.53 | <10 | ≤1 | ≥5.53 | >99.999% |

Virucidal activity tests were performed using hypochlorous acid against Polio Enterovirus 1 Sabin strain, Adenovirus type V and Orthopoxvirus. Polio Enterovirus 1, SABIN sock cultures were maintained on Vero cells, Adenovirus, type V, cultured on KB cells and Orthopoxvirus from the vaccine cultured on Vero cells. Viral suspensions (0.5 ml) were added to 0.5 ml of hypochlorous acid solution at a range of concentrations at 20° C. Viral suspensions were exposed to hypochlorous acid for 15, 30 and 60 minutes. Following incubation, all samples were serially diluted and viruses cultured according to standard procedures.

The effectiveness of hypochlorous acid against Norovirus (NV) and MS2 coliphage virus was evaluated using non-culturable human NV measured by RT-PCR and against two other surrogate viruses, coliphage MS2 and murine norovirus, detected by infectivity and RT-PCR. Norovirus, genetically characterized as genotype II.4. was obtained from patient's stools of an outbreak of gastroenteritis at the University of North Carolina campus in 2004. Stools were made into 1% stool suspensions in phosphate buffered saline (PBS, pH 7.5) on the day of an experiment. Bacteriophage MS2 was used as a surrogate for norovirus and cultivated using *E. coli* Famp (ATCC 700891). Murine norovirus a surrogate for human norovirus was obtained from the Skip Virgin lab in St. Louis and was cultivated by cell culture in Raw cells (ATCC TIB-71, Virginia, US). Virus suspensions (25 μl) consisting of 1% norovirus stool suspension and MS2 stock were treated with 1.2 ml of hypochlorous acid solution (20-200 ppm). After specified contact times, 25 μl of 6% sodium thiosulfate was added into 1.2 ml chlorine+ virus solution to neutralize any residual hypochlorous acid activity.

Broth cultures of either *M. terrae* (ATCC 15755) and *M. avium* (ATCC 15769) were grown for up to 35 days at 35° C. Mycobacteria suspensions (1 ml) were added to 1 ml of 0.3% BSA and 8 ml of hypochlorous acid solution at a range of concentrations at 20° C. After an exposure time of 5 minutes, 1 ml samples were neutralized using standard quench solution. The plates were incubated for 4-5 weeks at 35° C. and colonies counted.

Results shows that hypochlorous acid (40-180 ppm) effectively kills all organisms tested in the suspension Passes were achieved after 15 seconds contact time against *Pseudomonas aeruginosa, Staphylococcus aureus, Enterococcus faecium, Candida albicans, Aspergillus niger, Mycobacterium terrae* and *avium*. Passes were achieved after 5 minutes contact time against *Clostridium difficile* (spores), 60 minutes contact time against *Clostridium sporogenes, Bacillus subtilis* var. *niger, Bacillus cereus* endospores and 15 minutes contact time against Poliovirus Enterovirus 1, Adenovirus, type V, Orthopoxvirus from vaccine (Table 3 and Table 5). Additionally, suspension tests showed that exposure of human norovirus, murine norovirus and coliphage MS2 to hypochlorous acid solution at the dose range of 20-200 mg/L achieved 3 $\log_{10}$ reductions of both MS2 and human norovirus within a contact time of 20 seconds.

TABLE 5

Reduction in the number of surviving cells after contact time of 5 mins at 20° C. ± 1° C.

| Test Organism | Test Pass Requirement (Log reduction) | Test Result (Log reduction) |
| --- | --- | --- |
| *Pseudomonas aeruginosa* ATCC 15442 | $10^5$ in 60 minutes | $>10^5$ in 5 min. |
| *Staphylococcus aureus* ATCC 6538 | $10^5$ in 60 minutes | $>10^5$ in 5 min. |
| *Enterococcus faecium* ATCC 10541 | $10^5$ in 60 minutes | $>10^5$ in 5 min. |
| *Candida albicans* ATCC 10231 | $10^4$ in 60 minutes | $>10^4$ in 5 min. |
| *Aspergillus niger* ATCC 16404 | $10^4$ in 60 minutes | $>10^4$ in 5 min. |
| *Bacillus cereus* CIP 7 803 | $10^6$ in 60 minutes | $>10^6$ in 60 min. |
| *Bacillus subtilis* var. *niger* CIP 7 718 | $10^6$ in 60 minutes | $>10^6$ in 60 min. |
| *Clostridium sporogenes* CIP 7 939 | $10^6$ in 60 minutes | $>10^6$ in 60 min. |
| *Mycobacterium terrae* ATCC 15755 | $10^6$ in 60 minutes | $>10^5$ in 5 min. |
| *Mycobacterium avium* ATCC 15769 | $10^6$ in 60 minutes | $>10^5$ in 5 min. |
| Orthopoxvirus from vaccine | $10^4$ in 60 minutes | $>10^4$ in 15 min. |
| Adenovirus, type V | $10^4$ in 60 minutes | $>10^4$ in 15 min. |
| Poliovirus Enterovirus 1 | $10^4$ in 60 minutes | $>10^4$ in 15 min. |

Killing effect of hypochlorous acid solution and spray gel against *Propionibacterium acnes* measured in a $\log_{10}$ reduction assay Samples of hypochlorous acid solution (≤145 ppm AFC) and HOCl spray gel (40 ppm AFC) were tested against *Propionibacterium acnes* using 15-second or 5-minute contact times. They were found to produce a >5.00 log reduction and >99.999% percent reduction in the suspension test (Table 6).

TABLE 6

Test results for HOCl solution (≤145 ppm AFC) against *P. acnes*

| Contact time | Numbers Control Survivors | $\log_{10}$ | Test Sample Survivors | $\log_{10}$ | Log Reduction | % Reduction (% Kill) |
| --- | --- | --- | --- | --- | --- | --- |
| HOCl solution (≤145 ppm AFC) | | | | | | |
| 15-sec | $4.7 \times 10^6$ | 6.67 | <10 | ≤1 | ≥5.67 | >99.000% |
| 5-min | | | <10 | ≤1 | ≥5.67 | >99.000% |

TABLE 6-continued

Test results for HOCl solution (≤145 ppm AFC) against *P. acnes*

| Contact time | Numbers Control Survivors | $\log_{10}$ | Test Sample Survivors | $\log_{10}$ | Log Reduction | % Reduction (% Kill) |
| --- | --- | --- | --- | --- | --- | --- |
| Hypochlorous acid spray gel (40 ppm AFC) | | | | | | |
| 15-sec | $4.7 \times 10^6$ | 6.67 | <10 | ≤1 | ≥5.67 | >99.000% |
| 5-min | | | <10 | ≤1 | ≥5.67 | >99.000% |

Bactericidal, Fungicidal and Virucidal Carrier Tests

Carriers (glass slides) were inoculated with either *Salmonella cholerasuis, Pseudomonas aeruginosa* and Human influenza A, *Enterococcus faecium*, HIV, *Trichophyton mentagrophytes* or *Staphylococcus aureus*. These were then dried following the protocol guidelines and exposed to hypochlorous acid at <180 ppm for various contact times and cultured for viability.

For Norovirus and MS2 Coliphage Virus carrier tests, No. 4 polished stainless steel and ceramic tile were used as representative non-porous and porous surfaces, respectively. Virus suspensions (20 μl) consisting of 1% norovirus stool suspension (human Norovirus type II) and MS2 phage stock were spotted onto the center of each carrier surface in triplicate (i.e. three different squares per experiment). As a negative control, 20 μl of sterile PBS (pH 7.5) was spotted onto the carrier surface. The material was allowed to dry on each surface for 2-3 hours in a laminar flow hood. Individual surfaces were transferred with sterile forceps to 24 well plates. After specified contact times, 0.275 μl of 16% beef extract and 25 μl of 6% sodium thiosulfate were added into 1.2 ml chlorine solution to elute viruses and neutralize any residual hypochlorous acid activity. Plates were mixed for 20-minutes on a rotary device to facilitate virus elution from the test surfaces.

Tests passes (Table 7) were achieved after 2 minutes contact time against *Salmonella cholerasuis, Pseudomonas aeruginosa* and Human influenza A and after 5 minutes contact time *Enterococcus faecium*, HIV, *Trichophyton mentagrophytes* and *Staphylococcus aureus*. Additionally, carrier test results showed that hypochlorous acid on ceramic tiles and stainless steels inactivated MS2 and human norovirus by >3 $\log_{10}$ based on infectivity alone and infectivity and RNA testing, after 1 min of contact time with hypochlorous acid (20-200 ppm).

TABLE 7

Carrier Test Data

| Microorganism | Time to achieve pass |
| --- | --- |
| HIV-1 | 5 min. |
| *Enterococcus faecium* (VRE) | 5 min. |
| *Pseudomonas aeruginosa* | 2 min. |
| *Staphylococcus aureus* | 5 min. |
| *Salmonella cholerasuis* | 2 min. |
| *Trichophyton mentagrophytes* | 5 min. |
| Human Influenza A | 2 min. |

HOCl Verses Sulfamylon in the Management of Grafted Burn

Various antimicrobial agents have been used as protective agents over excised and grafted burn, with the primary benefit being infection prevention. However, many of these agents show considerable side effects such as sensitization.

A pilot study of HOCl (150-180 ppm AFC) effectiveness versus Sulfamylon 5% as an irrigant over excised and grafted burn, was conducted. A total of 19 patients were treated: 11 patients were treated with HOCl solution, and 8 patients in the control group were treated with Sulfamylon.

The primary evaluation was the equivalency of HOCl to Sulfamylon as an irrigant with microbial infection control. A secondary evaluation was the reduction in use of analgesics or a reduction in pain. Reduction of pain was evaluated using the John Hopkins visual analogue scale, daily, am and pm.

The study showed equivalency of HOCl solution (150-180 ppm) to one of the standard post grafting irrigation solutions, Sulfamylon, with regard to graft take and infection prevention. Further, pain reduction was better within the HOCl solution group. Both control and HOCl solution showed a similar safety profile, as indicated by the absence of adverse effects.

It was concluded that HOCl solution (150-180 ppm AFC) was effective by means of avoiding infection, reducing pain, promoting effective wound healing and providing conditions for damaged skin restoration and replacement.

Evaluation of Inflammation Reduction

In an investigator—blinded, randomized study, hypochlorous acid composition in the form of gel was evaluated for reduction of inflammation, by means of itching reduction. 30 subjects aged 12 to 75 years old with mild to moderate atopic dermatitis participated over a period of 3 days. The patients, 20 subjects, treated with hypochlorous acid composition, ≤450 ppm AFC, were compared to 10 untreated control subjects. The evaluation included an assessment of tolerability by investigator and participant.

Overall irritation, stinging, burning and itching on a 5-point ordinal scale were evaluated on day 1 (baseline visit), day 2 and day 3. Investigator assessment was calculated as the mean of 5-point scale for erythema, desquamation, lichenification, overall irritation, and excoriation. Subject queries were based on stinging, burning and itching at day 1, day 2, and day 3. Incidence of all adverse events, including serious adverse events, local skin reaction, and adverse events leading to discontinuation, were documented.

Treatment with the HOCl composition effectively reduced itch in subjects with mild to moderate atopic dermatitis as early as day 1.

The HOCl treatment group had significantly reduced itch compared with the Untreated group at Day 3 (p=0.007).

Treatment with the HOCl composition at least BID was very well tolerated, and there were no serious adverse events and no treatment-related discontinuations.

Case Study Evaluation of Inflammation Reduction

An evaluation of inflammation reduction by means of itching reduction and skin quality improvement was conducted on a 4 year old male treated with HOCl gel. The patient had eczema of the palmar aspect of the patient's hands and plantar aspect of the feet. The patient experienced severe itching, severe erythema (beet redness) to eschar formation, cracking, yellow plaques/hardening of skin and peeling of the skin over the course of two months. As a first line of therapy, the patient was prescribed Hydrocortisone Valerate Ointment USP, 0.2%, a topical corticosteroid twice daily to the affected areas. After 4 weeks of treatment twice daily with corticosteroids, the patient had no resolution of symptoms.

The patient was taken off the topical corticosteroid and instead treated with hypochlorous acid composition <450 ppm AFC, twice daily to the affected areas.

Treatment with HOCl composition effectively reduced symptoms in a subject with moderate eczema as early as Day 1.

At both Day 1 and Day 3, the patient exhibited marked reduction of symptoms including: reduction of itch, reduction of erythema (reduction of redness), skin wound healing (reduction of cracks), softening of plaques and movement towards normal skin color, and reduction of peeling.

Treatment with HOCl composition at least BID was very well tolerated.

The patient went on to complete resolution of all symptoms over the course of two weeks BID treatment.

There were no serious adverse events and no treatment related discontinuations.

The patient and guardian reported increased "ease-of-use" with the HOCl composition in form of gel vs treatment with corticosteroids, as there were no warnings regarding getting the product in/or near the eyes, nose or mouth, which is difficult when the product must be applied to the hands and fingers.

Modifications of the disclosed embodiments incorporating the spirit and substance of the invention may occur to persons skilled in the art and such modifications are within the scope of the present invention. All references cited herein are incorporated by reference in their entirety.

The invention claimed is:

1. A method for treating a patient having a nasal condition comprising a microbial infection and chronic inflammation, the method comprising:
    administering a hypochlorous acid formulation to an affected area of the nose of the patient, wherein the hypochlorous acid formulation has at least 250 ppm of available free chlorine and is at least 90% hypochlorous acid relative to the total concentration of hypochlorous acid, hypochlorite, and molecular chlorine.

2. The method of claim 1, wherein the chronic inflammation is a delayed-type hypersensitivity.

3. The method of claim 1, wherein the chronic inflammation is an immediate-type hypersensitivity.

4. The method of claim 1, wherein the condition is rhinitis, rhinorrhea, nasal congestion, or sinusitis.

5. The method of claim 4, wherein the hypochlorous acid formulation is delivered intranasally.

6. The method of claim 5, wherein the hypochlorous acid formulation comprises a nasal spray, nasal rinse, nasal cream or nasal gel.

7. The method of claim 1, further comprising additionally administering an effective amount of an antibiotic to treat the microbial infection.

8. The method of claim 1, wherein the hypochlorous acid formulation has a pH of from 5 to 6.5.

9. The method of claim 1, wherein the hypochlorous acid formulation has an available free chlorine content of from 250 ppm to 1000 ppm.

10. The method of claim 1, wherein the hypochlorous acid formulation has an available free chlorine content of from 250 ppm to 400 ppm.

11. The method of claim 1, wherein the hypochlorous acid formulation is administered to the affected area one to four times daily.

12. The method of claim 1, wherein the condition is allergic rhinitis.

* * * * *